United States Patent [19]

Berry et al.

[11] 4,429,409

[45] Jan. 31, 1984

[54] PORTABLE APPARATUS FOR ANALYZING METALS BY X-RAY FLUORESCENCE

[75] Inventors: Peter F. Berry; Wendell D. Miller; John L. Nethery, Jr., all of Austin, Tex.

[73] Assignee: Ramsey Engineering Company, St. Paul, Minn.

[21] Appl. No.: 435,854

[22] Filed: Oct. 21, 1982

Related U.S. Application Data

[63] Continuation of Ser. No. 216,229, Dec. 15, 1980.

[51] Int. Cl.³ .............................................. G01N 23/20
[52] U.S. Cl. .................................... 378/45; 340/146.2; 364/498; 378/48
[58] Field of Search ................. 378/45, 48; 340/146.2, 340/765, 805; 364/498, 527

[56] References Cited

U.S. PATENT DOCUMENTS 3,022,005 2/1962 Dickinson ........................ 340/146.2

OTHER PUBLICATIONS

Published Application Under the Patent Cooperation Treaty (PCT), International Publication No. WO80/01718, Inventor: Clark, Benton Clyde III, 37 pp. Specification, 10 Sheets Drawing, Priority Date of 9/02/79.

Primary Examiner—Alfred E. Smith
Assistant Examiner—T. N. Grigsby
Attorney, Agent, or Firm—Norvell & Associates

[57] ABSTRACT

A portable apparatus for analyzing a sample of material by the X-ray fluorescence method includes a hand-held probe unit connected to an electronic unit. The probe unit includes a radiation source for radiating the material sample and a radiation detector responsive to the X-ray radiation from the material sample for generating a plurality of sample signals representing the elements in the material sample. The probe and electronic units each include a universal asynchronous receiver transmitter for transmitting the sample signals from the probe unit to the electronic unit. The electronic unit includes random access memories for storing the sample signals and a library of groups of signals representing the elements of known materials. A keyboard is provided for adding signals to the library and/or storing the sample signals in the library. A microprocessor and associated circuitry compare the sample signals with the stored groups of signals and generate an identification signal if a match is found. A liquid crystal display and driving circuitry are responsive to the identification signal to generate an indication of the identity of the material sample. Additionally, the apparatus is adapted to permit elemental analysis of a given alloy sample.

10 Claims, 19 Drawing Figures

PORTABLE APPARATUS FOR ANALYZING METALS BY X-RAY FLUORESCENCE

This is a continuation of application Ser. No. 216,229 filed Dec. 15, 1980.

CROSS-REFERENCE TO RELATED APPLICATIONS

This application is related in subject matter to the following co-pending applications: Ser. No. 216,226, filed Dec. 15, 1980, entitled "Filter Means For An Apparatus For Analyzing Metals By X-Ray Fluorescence" (TN-13-PA-US) and Ser. No. 216,228, filed Dec. 15, 1980, entitled "Radiation Source Housing For An Apparatus For Analyzing Metals By X-Ray Fluorescence" (TN-14-PA-US), and assigned to the same assignee as this application.

BACKGROUND OF THE INVENTION

1. Field of the Invention

The present invention relates to a portable device for the identification of metal alloys by the X-ray fluorescence method.

2. Description of the Prior Art

Many businesses manufacture products from stock pieces of metal alloys purchased from a manufacturer of such stock. If several different alloys having a similar appearance are being stored and utilized in the daily manufacturing process, a mixed material problem can occur. If the wrong alloy is utilized in the manufacture of a part, it may result in the premature failure of the part during normal use. Such a failure has the potential for serious economic consequences and physical danger.

As businesses became aware of the mixed metals problem, they turned to quantitative inspection techniques including X-ray fluorescence. Many types of devices for X-ray flourescence analysis are known. Radiation is emitted by a sealed radioactive source and impinges upon the sample being tested. The radiation initiates the emission of secondary X-radiation from the sample. The secondary X-radiation is sensed and the concentration of any element in the sample is determined by the intensity of the characteristic X-rays of the element in the spectrum. Use can be made of special filters which make it possible to eliminate certain spectral lines so that only those that are typical of a given element are permitted to remain. Thus, by using a series of different filters, it is possible to determine the composition and concentration of the constituents of any sample.

U.S. Pat. No. 3,992,542 discloses an apparatus for the continuous analysis of samples. The apparatus includes a measuring head having a removable radioactive source and a counting assembly connected to the radiation detector. A sequential filter transfer unit has a conveyor driven in reciprocating motion between a filter stack and a gap between the source and the detector. A sample transfer unit with inclined parallel slide ramps and a receiving trough fitted with a push plate for passing the sample in front of the source in unitary sequence is controlled by a mechanical control assembly and an electronic assembly for recording signals delivered by the radiation detector after analysis of each sample. However, such a device has the disadvantage of requiring a sample to be brought to the device for analysis. Furthermore, the sample must be in a certain size range in order to be passed in front of the radioactive source.

SUMMARY OF THE INVENTION

The present invention concerns a portable apparatus for analyzing a sample of material by the X-ray fluorescence method. The apparatus includes a hand-held probe unit connected to an electronic unit. The probe unit has a radiation source for radiating the material sample and a radiation detector responsive to the X-ray radiation from the material sample for generating a plurality of sample signals representing the elements in the material. The sample signals are transmitted from the probe unit to the electronic unit through a pair of universal asynchronous receiver transmitters.

The electronic unit includes random access memories for storing the sample signals and a library of groups of signals representing the elements in known materials. The sample signals are compared with the stored groups and an identification signal is generated when a match is found. A display means includes a liquid crystal display and driving circuitry responsive to the identification signal for generating a visual indication of the identity of the sample. A keyboard is provided for adding signals to the library and/or storing the sample signals as an addition to the library. Additionally, the apparatus is adapted to permit elemental analysis of a given alloy sample.

DESCRIPTION OF THE PREFERRED EMBODIMENTS

The present invention relates to an apparatus for rapid, non-destructive on-site verification of type and elemental composition of important engineering alloys. The apparatus uses radioisotope excited X-ray fluorescence to analyze a sample in any one of a variety of physical forms, such as pipes, plates, welds, and welding materials, machined parts, castings, etc. The sample to be analyzed is exposed for a few seconds to radiation from a radioisotope source. The atoms of some elements in the material are caused to fluoresce and emit X-rays which are characteristic of the element. The detector system separates X-rays coming from the sample into discrete energy regions and, from a measure of the intensity in each region, determines the element concentrations. The energy regions corresponding to the elements: Ti, V, Cr, Mn, Fe, Co, Ni, Cu, Nb, Mo and W, are effectively analyzed.

Figure 1:
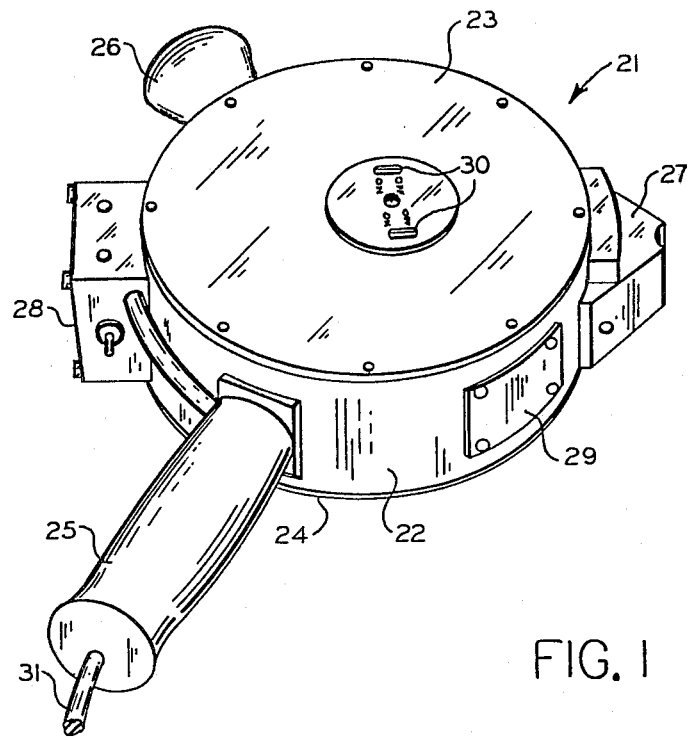
FIG. 1 is a perspective view of the probe of a metal analyzing apparatus according to the present invention.

There is shown in FIG. 1 a metal analyzing probe apparatus 21 according to the present invention. A radioistope source, a detector, and control circuitry are contained in a generally cylindrical housing 22. The housing has open upper and lower ends which are closed by a top cover 23 and a bottom cover 24 respectively which are attached to the sidewall of the housing by suitable fasteners. A handle 25 and a knob 26 are attached to the sidewall of the housing at spaced-apart positions to define an included angle of less than 180°. A source housing 27 and an end housing 28 are attached to the sidewall of the housing 22 and spaced approximately 180° apart. The source housing 27 and the end housing 28 are each approximately equally spaced between the handle 25 and the knob 26. As will be discussed below, a plate 29 is attached to the sidewall of the housing 22 to cover a filter access port and a pair of source shutter position tags 30 are positioned in the top cover 23. There is attached to the handle 25, electrical lines 31 which are connected to an electronic unit (not shown) including a power source for communication with and supplying power to the circuitry enclosed in the housing 22.

Figure 2:
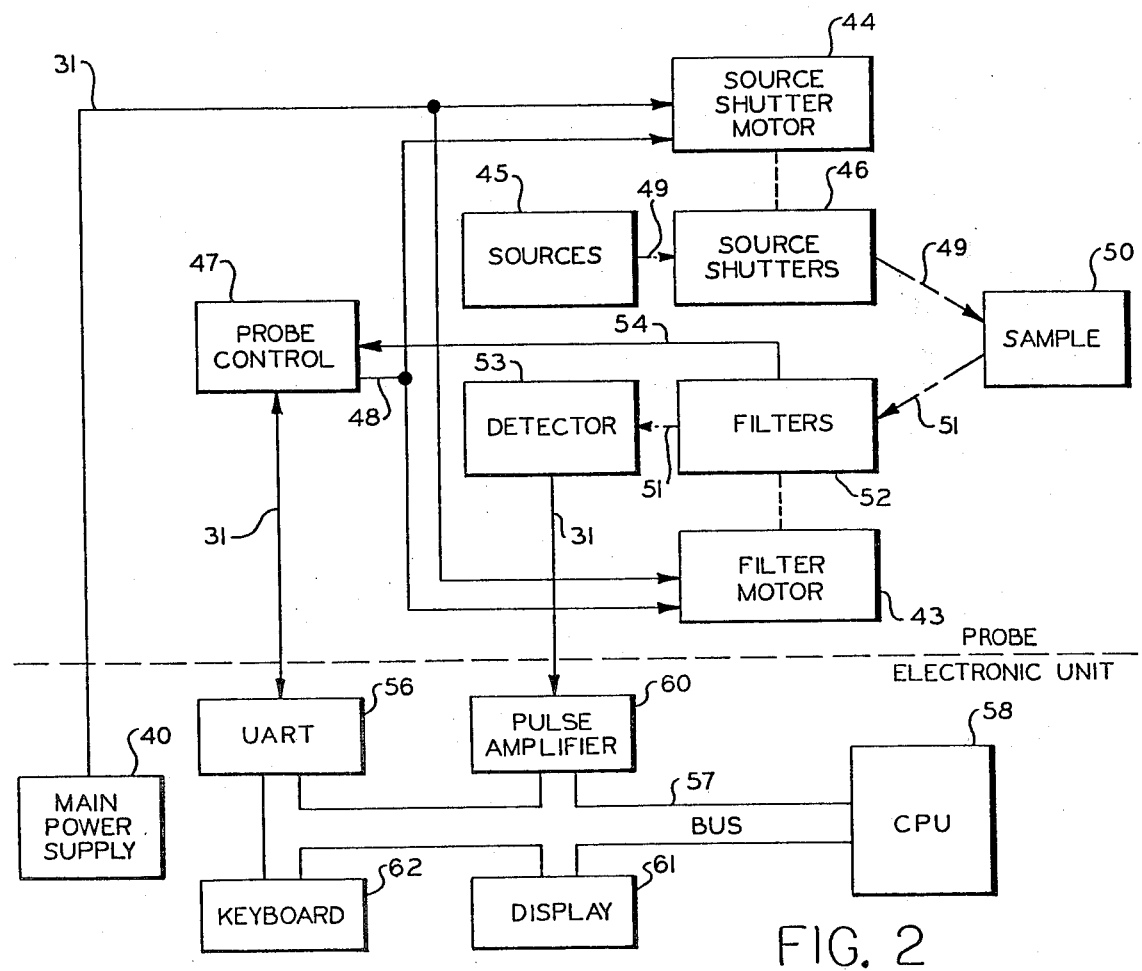
FIG. 2 is a block diagram of the metal analyzing apparatus according to the present invention.

A block diagram of the circuitry contained in the probe housing 22 of FIG. 1 and the associated electronic unit is illustrated in FIG. 2. A main power supply 40 in the electronic unit generates various voltages on the power lines 31. The line 31 is connected to a filter motor 43 and a source shutter motor 44.

The source housing 27 of FIG. 1 contains a pair of radioisotope sources 45. The sources 45 are positioned behind source shutters 46 which are mechanically controlled by the source shutter motor 44. A probe control circuit 47 generates control signals on a line 48 to actuate the source shutter motor 44 to open and close the source shutters 46. When the source shutters 46 are opened, radiation 49 from the sources 45 impinges upon a sample 50. X-rays 51 are emitted from the sample 50 and passed through one of a plurality of filters 52 to a detector 53. A signal representing the one of the filters 52 positioned between the sample 50 and the detector 53 is generated on a line 54 to the probe control circuit 47.

The probe control circuit 47 generates signals representing the operating conditions of the circuit on one of the lines 31 to a communications UART 56. The UART 56 is connected to a bus 57. Also connected to the bus 57 is a central processing unit CPU 58. The detector 53 generates an output signal on one of the lines 31 which is connected to a pulse amplifier 60. The pulse amplifier 60 generates an output signal to the bus 57. The output signal represents the X-ray intensity transmitted through one of the filters 52 to the detector 53. The CPU 58 reads the X-ray information and the filter identification from the bus lines 57. After the CPU 58 has read this information for one or more of the filters 52, it then determines the composition of the sample 50.

The CPU 58 includes a memory in which are stored the X-ray data from a plurality of alloys. The CPU compares the data for the sample 50 with the stored data until a match is found. If no match is found, the CPU 58 so indicates. The CPU 58 then generates output signals onto the bus 57 to a display 61 for a visual display of the identification of the alloy and its elemental contents. A keyboard 62 is connected to the bus 57 for communicating with the CPU 58 to generate control signals through the UART 56 to the probe control circuit 47. The probe control circuit 47 responds by controlling the filter motor 43 and the source shutter motor 44.

Figure 3:
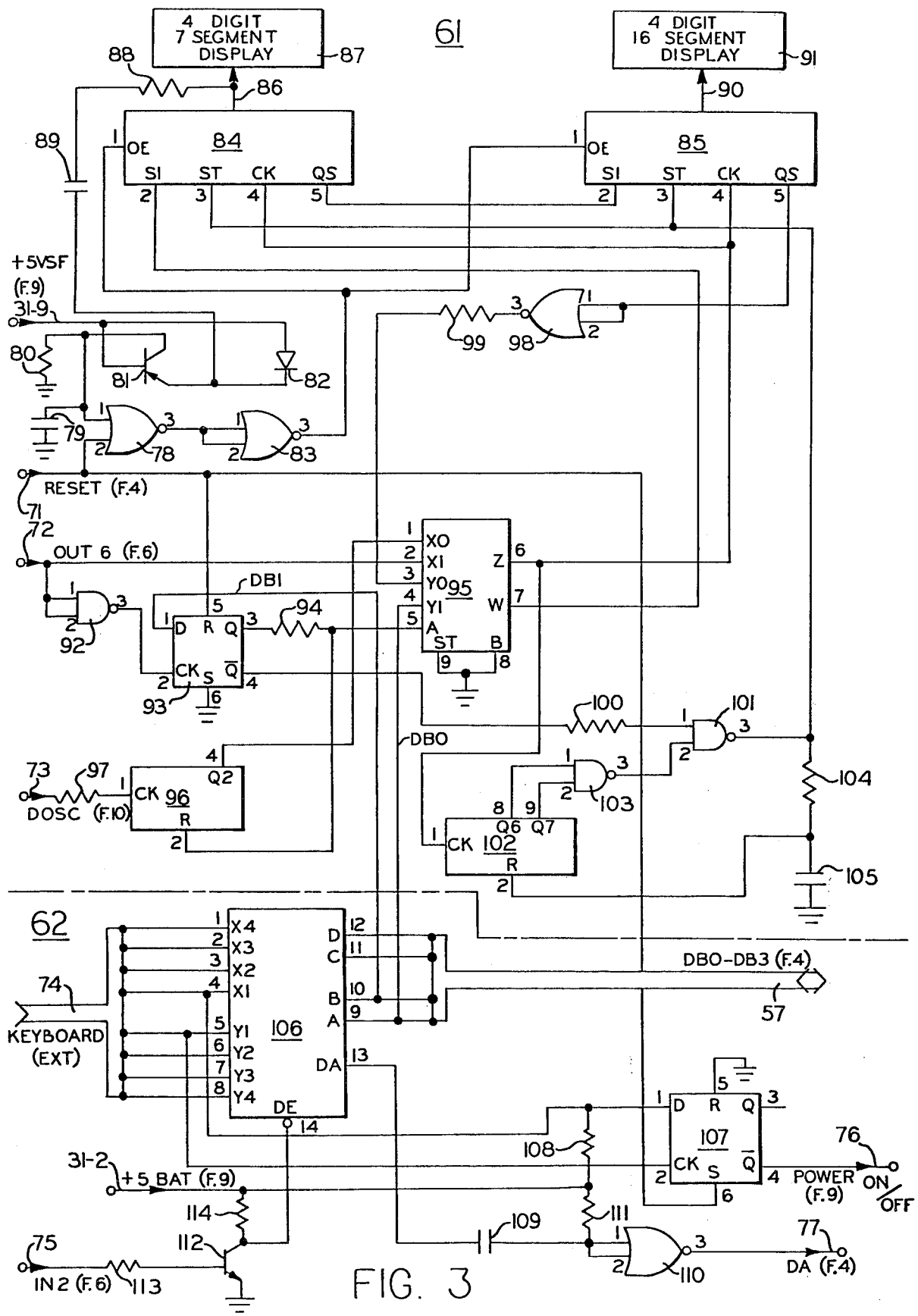
FIG. 3 is a schematic diagram of the display and interface for the keyboard shown in FIG. 2.

There is shown in FIG. 3, in schematic form, the display circuit 61 and an interface of the keyboard circuit 62. Input signals to FIG. 3 are RESET on a line 71, OUT6 on a line 72, DOSC on a line 73, KEYBOARD signals on a plurality of lines 74, and an IN2 signal on a line 75. Output signals from FIG. 3 are DB0–DB3 data signals on a portion of the bus 57, a POWER ON/OFF signal on a line 76, and a DA signal on a line 77. Power lines from the power supply are a +5VSF line 31-9 and a +5BAT line 31-2. Adjacent the name of each signal is an indication of the figure from which the signal has come or to which the signal is going.

The RESET signal line 71 is connected to an input 78-2 of a NOR gate 78. The NOR gate 78 has an input 78-1 connected to the circuit ground potential through a capacitor 79 and a resistor 80 connected in parallel. The input 78-1 is also connected to a collector of a PNP transistor 81. The transistor 81 has a base connected to the +5VSF power supply line 31-9 and an emitter connected to a cathode of a diode 82 having an anode connected to the base of the transistor.

An output 78-3 of the NOR gate 78 is connected to a pair of inputs 83-1 and 83-2 of a NOR gate 83. The NOR gate 83 has an output 83-3 connected to an OE input 84-1 of a shift register latch 84 and an OE input 85-1 of a shift register latch 85. The latch 84 is representative of four eight stage shift-and-store bus registers. An output line 86 is representative of four sets of eight output lines, each set of eight output lines being connected between the outputs of one of the registers and one of the segments of a four digit, seven segment display 87. The one of the output lines 86 connected to the backplane of the display 87 is also connected through a resistor 88 and a capacitor 89 to a cathode of the diode 82 to receive the +5VSF voltage. The latch 85 is representative of eight of the shift-and-store registers. A line 90 is representative of eight sets of eight lines each, with pairs of the sets being connected to the four digits of a four digit, sixteen segment display 91. Although not shown, the backplane of the display 91 is connected through the resistor 88 and the capacitor 89 to the cathode of the diode 82.

The OUT6 signal line 72 is connected to a pair of inputs 92-1 and 92-2 of the NAND gate 92. The NAND gate 92 has an output 92-3 connected to a clock input 93-2 of a D-type flip flop 93. The line 71 is connected to a reset input 93-5 of the flip flop 93. A non-inverting output 93-3 of the flip flop is connected through the resistor 94 to an A input 95-5 of a dual four channel-data selector 95 and a reset input 96-2 of a seven-stage ripple counter 96. The DOSC line 73 is connected through a resistor 97 to a clock input 96-1 of the counter 96. A Q2 output 96-4 of the counter 96 is connected to an X0 input 95-1 of the data selector 95.

The line 72 is also connected to an X1 input 95-2 of the data selector 95. The data selector 95 has a W output 95-7 which is connected to an SI input 84-2 of the registers 84. The input 84-2 is representative of the SI input for the least significant digit register. A QS output of the least significant digit register is connected to the SI input of the next most significant digit register. The four registers of the latch 84 are connected together in series in this manner and a QS 84-5 output of the most significant digit register is connected to a SI input 85-2 of the first register in the least significant digit pair of the latch 85. The eight registers in the latch 85 are also connected in series from the QS outputs to the SI inputs and the last register has a QS output 85-5 which is connected to a pair of inputs 98-1 and 98-2 of an NOR gate 98. The gate 98 has an output 98-3 which is connected through a resistor 99 to a Y0 input 95-3 of the data selector 95.

The data selector 95 has a Z output 95-6 which is connected to a clock input of each of the registers represented by a pair of clock inputs 84-4 and 85-4. The flip flop 93 has an inverting output 93-4 which is connected through a resistor 100 to an input 101-1 of a NAND gate 101. The NAND gate 101 has an output 101-3 connected to a ST input of each of the registers represented by a pair of inputs 84-3 and 85-3. The Z output 95-6 of the data selector 95 is connected to a clock input 102-1 of a seven-stage ripple counter 102. The counter 102 has a Q6 output 102-8 connected to an input 103-1 of the NAND gate 103, and a Q7 output 102-9 connected to an input 103-2 of the gate 103. The gate 103 has an output 103-3 connected to an input 101-2 of the NAND gate 101. The output 101-3 of the gate 103 is connected through a resistor 104 and a capacitor 105 to the ground potential of the circuit. The junction of the resistor 104 and the capacitor 105 is connected to a reset input 102-2 of the counter 102.

The keyboard lines 74 are connected to the X1–X4 and Y1–Y4 inputs of a keyboard encoder 106. When a keyboard key is depressed, a signal is generated on one of the X lines and on one of the Y lines to identify the key. These signals are encoded as a binary number on a set of output lines 106-9 through 106-12. The output line 106-9 is connected to a Y1 input 95-4 of the data selector 95. The output line 106-10 is connected to a D input 93-1 of the flip flop 93. The lines 106-9 through 106-12 are connected to the DB0–DB3 signal lines in the bus lines 57. The keyboard line connected to the X1 input 106-4 is also connected to a D input 107-1 of a D-type flip flop 107. The input 107-1 is also connected through a resistor 108 to the +5BAT power supply line 31-2. The one of the keyboard lines 74 connected to a Y1 input 106-5 is also connected to a clock input 107-2 of the flip flop 107. An inverting output 107-4 is connected to the POWER ON/OFF line 76. A reset input 107-5 of the flip flop is connected to the circuit ground potential and a set input 107-6 is connected to the RESET signal line 71.

A DA output 106-13 of the keyboard encoder 106 is connected through a capacitor 109 to a pair of inputs 110-1 and 110-2 of a NOR gate 110. The inputs of the NOR gate are also connected through a resistor 111 to the +5BAT power supply. An output 110-3 of the gate 110 is connected to the DA signal line 77. A DE input 106-14 of the keyboard encoder 106 is connected to a collector of an NPN transistor 112. The IN2 signal line 75 is connected through a resistor 113 to a base of the transistor 112. An emitter of the transistor 112 is connected to the circuit ground potential and the collector of the transistor 112 is connected through a resistor 114 to the +5BAT power supply.

The displays 87 and 91 are utilized to visually output data generated by the CPU 58 of FIG. 2. A logic "1" RESET signal on the line 71 will be transmitted through the gate 78 and inverted by the gate 83 to enable the output of the registers 84 and 85. The RESET signal also resets the flip flops 93 and 107. When the CPU is ready to transmit data to be displayed, it generates an OUT6 signal on the line 72 and the DB0 and DB1 signals on the bus 57. The OUT6 signal clocks the DB1 data bit from the input 93-1 to the non-inverting output 93-3 of the flip flop 93. The DB1 data bit is thus applied to the A input 95-5 to select the inputs 95-2 and 95-4 of the data selector 95. The OUT6 signal is generated at the Z output 95-6 to clock the registers 84 and 85. The DB0 signal is generated at the W output 97-7 and is the data bit which is clocked into the first position of the first one of the registers 84.

The CPU clocks in ninety-six data bits to fill all the positions in the registers 84 and 85. Then the DB1 data bit is changed to logic "0" and clocked through the flip flop 93 to switch the state of the data selector 95. Now the signal at the input 95-1 will appear at the output 95-6 and the signal at the input 95-3 will appear at the output 95-7. The DOSC signal on the line 73 is divided by two by the ripple counter 96 to generate a clock signal at the input 95-1 which is transmitted through the data selector to the clock inputs of the shift registers 84 and 85. These data bits are inverted by the gate 98 and appear at the output 95-7 to be clocked back into the first position of the first one of the shift registers 84. Thus, a series of ninety-six clock pulses generated by the ripple counter 96 will cause all of the data bits from the shift registers 84 and 85 to be inverted and placed back into the shift registers. This circuit is known as a twisted ring counter and is utilized to generate the data bits as AC signals for driving the displays 87 and 91. The junction of the resistor 104 and the capacitor 105 is connected to a reset input 102-2 of the counter 102.

After the ninety-six signals have been clocked through the twisted ring counter, the ripple counter 102 generates an output signal through the gates 103 and 101 to latch the data at the output lines 86 and 90. This process is continuously repeated to alternate the signals at the output lines 86 and 90 between logic "0" and logic "1" to generate the AC signals for the displays.

The displays 87 and 91 can be damaged if the AC signal is removed. If any one of the shift registers fails, a pump circuit connected to the backplane output line turns off the shift registers to protect the displays. As was previously stated, the backplane signal is transmitted through the resistor 88 and the capacitor 89 to the emitter of the transistor 81 which is turned on. Thus, a positive potential signal appears at the collector of the transistor 81 and is inverted by the gates 78 and 83 to supply a positive potential signal to the output enable inputs 84-1 and 85-1. If any shift register fails, the backplane signal will disappear and the transistor 81 will remove the output enable signal to remove the output signals from the lines 86 and 90 thereby protecting the displays 87 and 91.

The keyboard is an X-Y matrix. When a key is depressed, an X and a Y signal are generated on the lines 74. The keyboard encoder 106 responds to the generation of such signals by generating a signal at the data available output 106-13 which signal is then generated on the line 77 to the CPU. The CPU responds by generating the IN2 signal on the line 75 to turn on the transistor 112 and enable the keyboard encoder at the data enable input 106-14. The X and Y signals are encoded at the outputs 106-9 through 106-12 which are connected to the bus 57. Thus, the CPU can read the encoded signals from the bus 57 to determine which key has been pressed.

If the apparatus has been turned off, an on/off power key is depressed to generate the X1 and Y1 signals. These signals are connected to the flip flop 107 which clocks the inverse of the X1 signal to the inverting output 107-4 in response to the Y1 signal at the clock input 107-2. Thus, a POWER ON/OFF signal is generated on the line 76 to the power supply to turn on or off the power for the apparatus.

In summary, the circuit shown in FIG. 3 includes a twisted ring counter for receiving serial data from the CPU for display. The twisted ring counter circulates the data to generate an AC signal for driving the displays. Inputs from the keyboard are encoded and generated to the CPU on the data bus.

Figure 4:
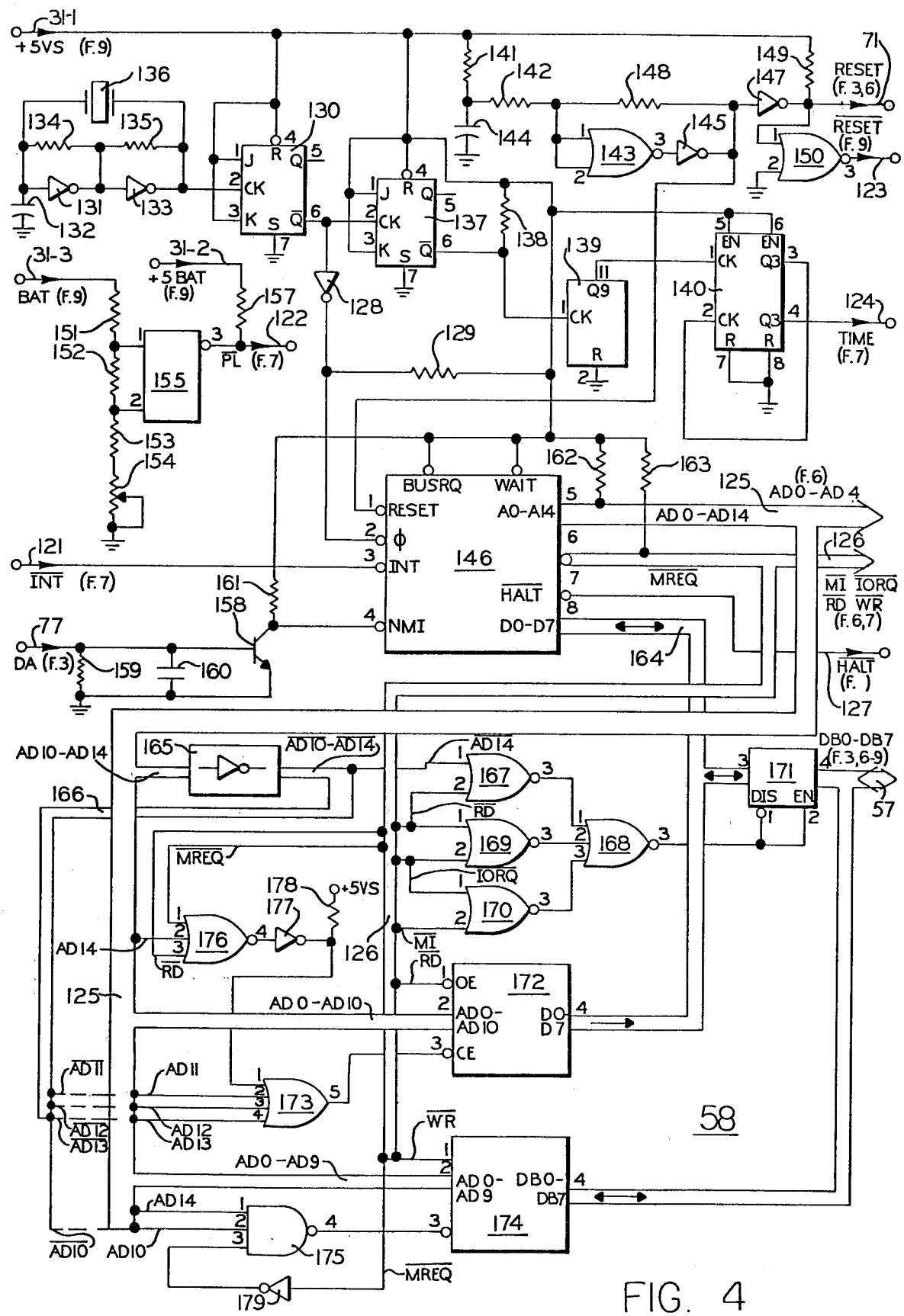
FIG. 4 is a schematic diagram of the CPU shown in FIG. 2.

There is shown in FIG. 4 a schematic diagram of the CPU 58 of FIG. 2. Inputs to the circuits of FIG. 4 are a +5VS power supply line 31-1, the +5BAT power supply line 31-2, a BAT power supply line 31-3, an $\overline{INT}$ signal line 121, and the DA signal line 77. Outputs from the circuits of FIG. 4 are a $\overline{PL}$ signal line 122, the RESET signal line 71, a $\overline{RESET}$ signal line 123, a $\overline{TIME}$ signal line 124, an address bus having lines 125 for address signals AD0-AD4, a control signals bus 126 having lines for signals $\overline{MI}$, $\overline{IORQ}$, $\overline{RD}$, and $\overline{WR}$, a $\overline{HALT}$ signal line 127, and the data bus lines 57 for the signals DB0-DB7.

The power supply line 31-1 is connected to a reset input 130-4, a J input 130-1 and a K input 130-3 of J-K type flip flop 130. An input of an inverter 131 is connected to the circuit ground potential through a capacitor 132. An output of the inverter 131 is connected to an input of an inverter 133 which has an output connected to a clock input 130-2 of the flip flop 130. A resistor 134 is connected between the input and the output of the inverter 131 and a resistor 135 is connected between the input and the output of the inverter 133. A crystal 136 is connected between the input of the inverter 131 and the output of the inverter 133.

The flip flop 130 has an inverting output 130-6 connected to a clock input 137-2 of a J-K type flip flop 137. The power supply line 31-1 is connected to a J input 137-1, a K input 137-3, and a reset input 137-4 of the flip flop 137. The flip flop 137 has an inverting output 137-6 which is connected through a resistor 138 to the power supply line 31-1 and to a clock input 139-1 of a seven stage ripple counter 139. The ripple counter has a reset input 139-2. Which is connected to the circuit ground potential and a Q9 output 139-11 which is connected to a first clock input 140-1 of a dual BCD up counter 140.

A Q3 output 140-3 is connected to a second clock input 140-2 of the counter 140. A second Q3 output 140-4 is connected to the $\overline{TIME}$ signal line 124. A pair of enable (EN) inputs 140-5 and 140-6 are connected to the power supply line 31-1 to continuously enable the counter 140.

The power supply line 31-1 is connected through a pair of series connected resistors 141 and 142 to a pair of inputs 143-1 and 143-2 of a NOR gate 143. The junction of the resistors 141 and 142 is connected to the circuit ground potential through a capacitor 144. The NOR gate 143 has an output 143-3 which is connected through an inverter 145 to a reset input 146-1 of a microprocessor 146. The output of the inverter 145 is also connected through an inverter 147 to the RESET line 71. A resistor 148 is connected between the inputs of the NOR gate 143 and the output of the inverter 145. The power supply line 31-1 is connected to the RESET line 71 through a resistor 149. The line 71 is also connected to an input 150-1 of a NOR gate 150 having a second input 150-2 connected to the circuit ground potential. The NOR gate 150 has an output 150-3 connected to the $\overline{RESET}$ line 123.

The power supply line 31-3 is connected to the circuit ground potential through series connected resistors 151, 152, 153, and a potentiometer 154. A junction between the resistors 151 and 152 is connected to an input 155-1 of a micropower level detector 155. A junction between the resistors 152 and 153 is connected to a second input 155-2 of the level detector 155. The level detector 155 has an inverting output 155-3 which is connected to the $\overline{PL}$ signal line 122. The power supply line 31-2 is connected through a resistor 157 to the line 122.

The inverting output 130-6 of the flip flop 130 is connected to a clock input 146-2 of the microprocessor 146. The line 121 is connected to an interrupt input 146-3 of the microprocessor 146. The line 77 is connected to a base of an NPN transistor 158 having a collector connected to an NMI input 146-4 of the microprocessor 146. The line 77 is also connected to the circuit ground potential through a resistor 159 connected in parallel with a capacitor 160. An emitter of the transistor 158 is connected to the circuit ground potential and the collector is connected to the power supply line 31-1 through a resistor 161.

The microprocessor 146 has a plurality of address outputs 146-5 which are connected to the address signal bus 125. Each of the address bus lines is connected to the power supply line 31-1 through a resistor such as a representative resistor 162. The microprocessor 146 also generates a plurality of control signals such as $\overline{MREQ}$, $\overline{MI}$, $\overline{IORQ}$, $\overline{RD}$, and $\overline{WR}$ at a plurality of outputs represented by an output 146-6 connected to the bus 126. Each of the bus lines is connected to a power supply line 31-1 through a resistor such as a representative resistor 163. The microprocessor 146 also generates a $\overline{HALT}$ signal at an output 146-7 which is connected to the line 127. The microprocessor generates and receives data signals at a plurality of bidirectional ports represented by a port 146-8 which is connected to a bidirectional data bus 164. The resistors 162 and 163 are pull-up resistors which maintain the address bus lines 125 and the control signal bus lines 126 at the CMOS voltage level.

The AD10-AD14 lines of the address bus 125 are connected to the inputs of a plurality of inverters 165 to generate $\overline{AD10}$-$\overline{AD14}$ address signals on an inverted address bus 166. An AD14 address signal bus line is connected to an input 167-1 of a NOR gate 167. An input 167-2 of the gate 167 is connected to the $\overline{RD}$ signal line of the control signal bus 126 and an output 167-3 of the gate 167 is connected to an input 168-1 of a NOR gate 168. The $\overline{RD}$ signal line is also connected to an input 169-1 of a NOR gate 169 having a second input 169-2 connected to the $\overline{IORQ}$ signal line of the bus 126. The NOR gate 169 has an output 169-3 connected to an input 168-2 of the gate 168. $\overline{IORQ}$ signal line is also connected to an input 170-1 of a NOR gate 170 having an output 170-3 connected to an input 168-3 of the NOR gate 168. The gate 170 has a second input 170-2 which is connected to the $\overline{MI}$ signal line of the signal bus 126. The NOR gate 168 has an output 168-3 connected to a disable input 171-1 and an enable input 171-2 of a level shifter 171. Bidirectional ports 171-3 of the level shifter 171 are connected to the data bus 164 and a plurality of bidirectional ports 171-4 are connected to the data bus 57.

A memory 172 has an output enable input 172-1 connected to the $\overline{RD}$ control signal line of the control signal bus 126. The memory 172 also has a plurality of address inputs 172-2 which are connected to the address bus 125 to receive the signals AD0–AD10. The memory 172 also has a chip enable input 172-3 connected to an output 173-5 of an OR gate 173. The memory 172 has a plurality of outputs 172-4 which are connected to the data bus 164. The memory 172 can be formed from a plurality of eraseable programmable read only memories (EPROMs).

A memory 174 has a write input 174-1 connected to the $\overline{WR}$ signal line of the control signal bus 126. The memory 174 has a read input 174-3 connected to an output 175-4 of a NAND gate 175. The memory 174 has a plurality of address inputs 174-2 which are connected to the address bus 125 to receive the address signals AD0–AD9. The memory 174 has a plurality of bidirectional ports 174-4 which are connected to the data bus 57. The memory 174 can be comprised of a plurality of random access memories (RAMs). A NOR gate 176 has an input 176-1 connected to the control signal bus 126 to receive the $\overline{MREQ}$ signal. An input 176-2 is connected to the address bus to receive the address signal AD14 and an input 176-3 is connected to the control signal bus 126 to receive the signal $\overline{RD}$. An output 176-4 of the NOR 176 is connected through an inverter 177 to an input 173-1 of the OR gate 173. The input 173-1 is also connected to the power supply line 31-1 through a resistor 178. The OR gate 173 has an input 173-2 connected to receive the AD11 address signal, an input 173-2 connected to receive the AD12 address signal, and an input 173-4 connected to receive the AD13 address signal from the address bus 125. The NAND 175 has an input 175-1 connected to receive the AD14 address signal and an input 175-2 connected to receive the AD10 address signal. The $\overline{MREQ}$ control line of the control signal bus 126 is connected through an inverter 179 to an input 175-3 of the NAND gate 175.

The OR gate 173 is representative of an individual OR gate for each of the memories included in the read only memory 172. There are eight possible combinations of $\overline{AD11}$–$\overline{AD13}$ and AD11–AD13 signals. Thus, up to eight read only memories can be controlled using the aforementioned six address signals. The NAND 175 is representative of two such NAND gates for controlling up to four random access memories in the memory 174. The signals AD10 and $\overline{AD10}$ are utilized to select one of the NAND gates which are connected to a pair of the random access memories, each random access memory having four of the eight data ports 174-4.

The crystal 136, the resistors 134 and 135, the inverters 131 and 133 and the capacitor 132 form a 4.096 MHz clock which generates a train of clock pulses at the clock input 130-2 of the flip flop 130. The flip flop 130 divides this pulse train by two to generate a 2.048 MHz clock signal at the clock input 146-2 of the microcprocessor. This clock signal defines the operating frequency of the microprocessor system. The clock signal is further divided by the flip flop 137, the counter 139, and the counter 140 to generate the TIME signal on the line 124 at a period of fifty milliseconds.

The level detector 155 monitors the battery voltage on the line 31-3. The battery is the main power supply for the apparatus. When the battery voltage falls to a predetermined level, typically 5.5 volts, the level detector 155 will generate the $\overline{PL}$ signal on the line 122. This signal is utilized to shut down the apparatus while maintaining any data which may have been stored in the random access memories.

The microprocessor 146 executes a program which is stored as instructions in the EPROMs 172. The microprocessor generates address signals on the address bus 125 to address storage locations in the memory 172. The memory 172 outputs the data bits in the addressed storage positions onto the data bus 164 to the microprocessor at the data ports 146-8. The microprocessor also generates bits on the data bus 164 through the level shifter 171 and onto the bus 57. The level shifter 171 converts the TTL signals from the microprocessor 146 into CMOS level signals for use by the other circuitry in the apparatus. The microprocessor 146 can also generate address signals on address bus 125 to the RAMs 174 to read data from the bus 57 or write data onto the bus 57 utilizing the storage locations in the RAMs.

When the apparatus is turned on, voltage will be applied to the line 31-1 and the capacitor 144 will begin to charge through the resistor 141. However, before the capacitor has fully charged, a logic "0" will be applied to the inputs of the NOR gate 143 to generate a logic "1" at the output 143-3. The inverter generates a logic "0" signal to reset the microprocessor 146 at the reset input 146-1 and the inverter 147 generates a logic "1" RESET signal on the line 71 to the other circuitry. When the capacitor 144 has charged, the reset signals are removed and the microprocessor 146 begins to execute the program.

The generation of an interrupt signal INT on the line 121 will signal the microprocessor to interrupt the execution of the program and perform a task as will be discussed below. The generation of the DA signal on the line 77 turns on the transistor 158 to generate an interrupt signal at the NMI input 146-4. This operation signals the microprocessor 146 that a key on the keyboard has been depressed and that the microprocessor should read the data bits representing the key position from the bus lines 57.

The NOR gates 167, 168, 169 and 170 control the level shifter 171. If one or more of the signals $\overline{AD14}$, $\overline{RD}$, $\overline{IORQ}$ and $\overline{MI}$ are not being generated at logic "0", the NOR gate 168 will generate a logic "1" to enable the level shifter to pass data signals. If all of the aforementioned signals are present, the level shifter 171 is disabled and the RAM 174 other input-output signals are connected to the bus 57. When the microprocessor 146 requires an instruction from the memories 172, a read $\overline{RD}$ signal and a memory request $\overline{MREQ}$ signal are generated. The read signal enables the memories 172 at the input 172-1 and the read signal and the memory request signal enable the NOR gate 176. In the absence of the AD14 signal, the NOR gate 176 generates a logic "1" signal which is inverted by the inverter 177 to enable the OR gate 173. The OR gate 173 represents the OR gate associated with the EROM to be read and the required address signals are generated by the microprocessor 146 to generate an enabling signal at the input 172-3. The selected EPROM generates the data bits selected by the address signals AD0–AD10 and outputs these data bits on the data bus 164 to the microprocessor 146.

When it is desired to read data from the RAMs 174, the MEMRQ signal is generated and inverted by the inverter 179 to enable the NAND gate 175. The desired RAM is selected with the associated address bits to generate an enabeling logic "0" from the NAND 175. The WR signal is generated at logic "1" to select the read function and the appropriate address bits are generated at the input 174-2 to cause the data bits to be generated at the ports 174-4 onto the bus 57 and through the level shifter 171 to the microprocessor 146 on the data bus 164. When it is desired to write data into the RAMs 174, the WR signal is generated at logic "0" to select the write function and the address signals at the input 174-2 will select the address locations into which are written the data bits on the bus 57.

In summary, the microprocessor 146 executes program instructions stored in EPROMs 172 to control the apparatus according to the present invention. The microprocessor 146 also controls a random access memory 174 for reading data from or writing data to the bus 57. The circuit shown in FIG. 4 also includes the system clock which defines the time base for the microprocessor and a power level detector which monitors the main power supply battery.

Figure 5:
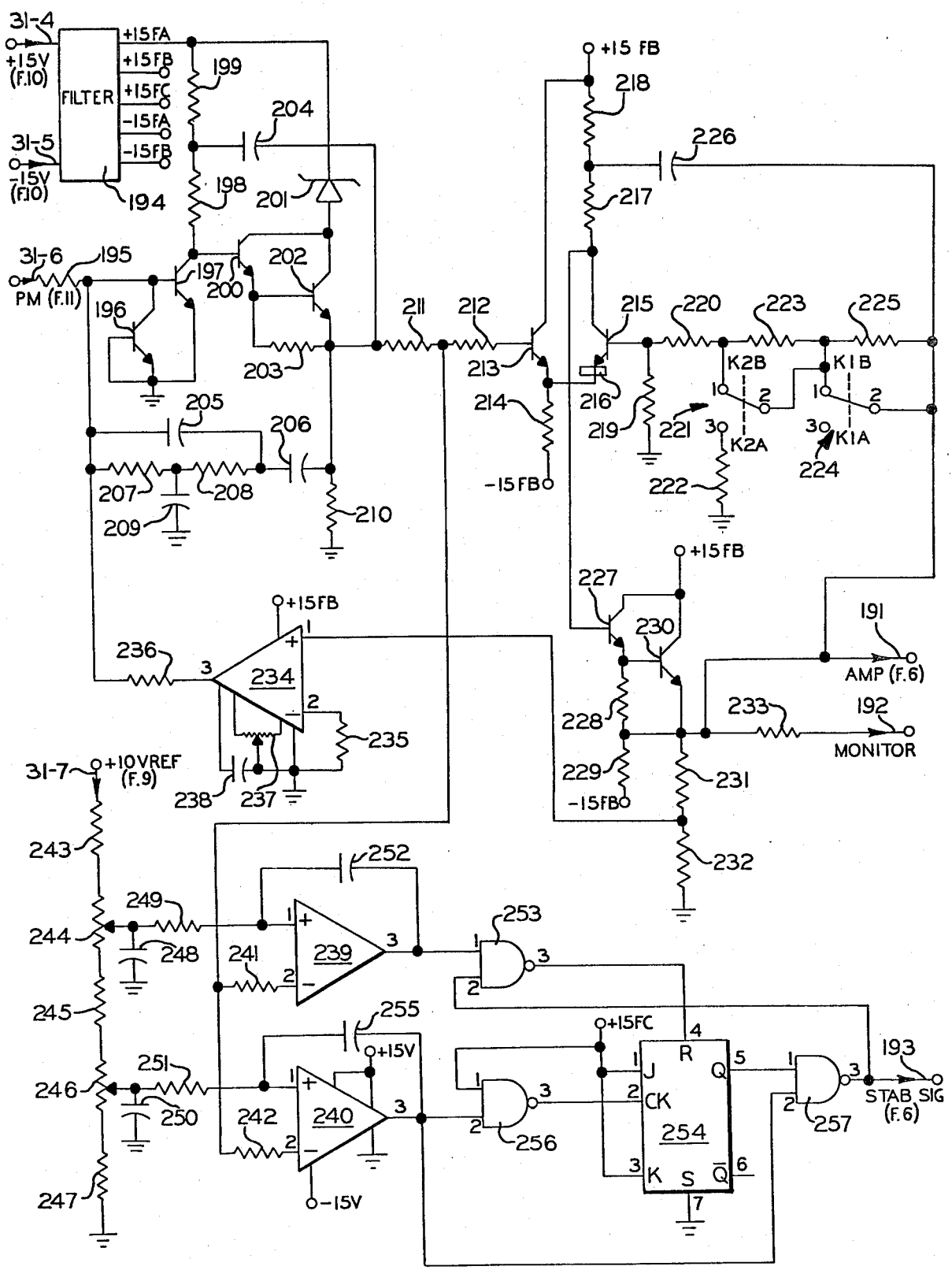
FIG. 5 is a schematic diagram of the pulse amplifier shown in FIG. 2.

There is shown in FIG. 5 a schematic diagram of the pulse amplifier 60 of FIG. 2. Inputs to the pulse amplifier circuit are a +15V power supply voltage on a line 31-4, a −15V power supply voltage on a line 31-5, a +10VREF power supply voltage on a line 31-7 and a PM signal on a line 31-6. Outputs from the circuit are an AMP signal on a line 191, a MONITOR signal on a line 192, and a STAB SIG on a line 193.

The lines 31-4 and 31-5 are connected to a filter circuit 194 which is representative of a plurality of noise filters comprising several resistors and capacitors connected to the ground potential. The individual components are not shown in the interest of clarity. Filtered voltage outputs from the filter 194 are +15FA, +15FB, +15FC, −15FA, and −15FB. These voltages are supplied to several elements in the circuits of FIG. 5 and FIG. 6.

The line 31-6 is connected though a resistor 195 to a collector of an NPN transistor 196 and a base of an NPN transistor 197. The transistor 196 has a base and an emitter connected to the ground circuit potential and the transistor 197 has an emitter connected to the ground circuit potential and a collector connected to the +15FA output voltage from the filter 194 through a pair of series connected resistors 198 and 199. The collector of the transistor 197 is also connected to a base of an NPN transistor 200 having a collector connected to an anode of a zener diode 201. The zener diode has a cathode connected to the +15FA power supply and its anode is connected to a collector of an NPN transistor 202. An emitter of a transistor 200 is connected to a base of the transistor 202 and through a resistor 203 to an emitter of the transistor 202. The emitter of the transistor 202 is also connected through a capacitor 204 to the junction of the resistors 198 and 199. The base of the transistor 197 is connected through a pair of series connected capacitors 205 and 206 to the emitter of the transistor 202. A pair of series connected resistors 207 and 208 are connected across the capacitor 205 and a capacitor 209 is connected at the junction of the resistors 207 and 208 to the circuit ground potential. A resistor 210 is connected between the emitter of the transistor 202 and the circuit ground potential.

The emitter of the transistor 202 is connected through a pair of series connected resistors 211 and 212 to a base of an NPN transistor 213. The transistor 213 has a collector connected to the +15FB power supply and an emitter connected through a resistor 214 to the −15FB power supply. The emitter of an NPN transistor 213 is connected to an emitter of an NPN transistor 215 with the connection passing through a ferrite bead 216. The transistor 215 has a collector connected through a pair of series connected resistors 217 and 218 to the +15FB power supply. The transistor 215 has a base connected through a resistor 219 to the circuit ground potential and through a resistor 220 to a fixed terminal 221-1 of a K2 relay. A second fixed terminal 221-3 of the K2 relay is connected through a resistor 222 to the circuit ground potential. The terminal 221-1 is connected through a resistor 223 to a movable terminal 221-2 of the K2 relay. The terminal 221-2 is also connected to a first fixed terminal 224-1 of a K1 relay. The terminal 224-1 is also connected through a resistor 225 to a movable terminal 224-2 of the K1 relay. The terminal 224-2 is connected through a capacitor 226 to the junction of the resistors 217 and 218 and to the AMP signal line 191.

The collector of transistor 215 is connected to a base of an NPN transistor 227 having a collector connected to the +15FB power supply. The transistor 227 has an emitter connected through a pair of series connected resistors 228 and 229 to the −15FB power supply. The emitter of the transistor 227 is also connected to a base of an NPN transistor 230 having a collector connected to the +15FB power supply. The transistor 230 has an emitter connected through a pair of series connected resistors 231 and 232 to the circuit ground potential. The emitter of the transistor 230 is also connected to the AMP line 191 and through a resistor 233 to the MONITOR line 192. The junction of the resistors 231 and 232 is connected to a non-inverting input 234-1 of an operational amplifier 234. The amplifier 234 has an inverting input 234-2 connected through a resistor 235 to the circuit ground potential. An output 234-3 of the amplifier 234 is connected through a resistor 236 to the base of the transistor 197. A balance potentiometer 237, the +15FB power supply, and a compensating capacitor 238 are connected to the appropriate terminals of the operational amplifier 234.

The junction of the resistors 211 and 212 is connected to a pair of inverting inputs 239-2 and 240-2 of a pair of differential voltage comparators 239 and 240 respectively through a pair of resistors 241 and 242 respectively. The line 31-7 is connected to the circuit ground potential through series connected resistor 243, potentiometer 244, resistor 245, potentiometer 246 and resistor 247. A tap on the potentiometer 244 is connected to the circuit ground potential through a capacitor 248 and to a non-inverting input 239-1 of the comparator 239 through a resistor 249. A tap of the potentiometer 246 is connected to the circuit ground potential through a capacitor 250 and to a non-inverting input 240-1 of the comparator 240 through a resistor 251.

An output 239-3 of the comparator 239 is connected to the non-inverting input 239-1 through a capacitor 252 and to an input 253-1 of the NAND gate 253. The NAND 253 has an input 253-2 connected to the line 193 and an output 253-3 connected to a reset input 254-4 of a J-K type flip flop 254. The amplifier 240 has an output 240-3 which is connected to the non-inverting input 240-1 through a capacitor 255, to an input 256-2 of a NAND gate 256, and to an input 257-2 of a NAND gate 257. The +15FC power supply is connected to an input 256-1 of the NAND 256, and to a J input 254-1 and to a K-input 254-3 of the flip flop 254. The NAND 256 has an output 256-3 connected to a clock input 254-2 of the flip flop 254. A non-inverting output 254-5 of the flip flop 254 is connected to an input 257-1 of the NAND 257. The NAND 257 has an output 257-3 connected to the line 193.

The PM signal is pre-amplified by the transistors 196, 197, 200 and 202. The pre-amplified signal is then inputed to a voltage amplifier comprising the transistors 213 and 215 to generate an output signal through the Darlington pair 227 and 230 as the AMP signal on the line 191. The gain of the voltage amplifier can be set by selecting combinations of the feedback resistors 222, 223 and 225. The selection of the resistors is controlled by the K1 and K2 relays which will be discussed below. The operational amplifier 234 is a DC restorer which maintains the line 191 at the circuit ground potential between pulses no matter what the pulse rate is.

The comparators 239 and 240 compare the preamplifier output signal with predetermined voltage levels to generate the STAB SIG on the line 193. The signal on the line 193 is utilized to maintain the high voltage input to the photomultiplier tube in the detector 53 of FIG. 2 at a predetermined voltage level regardless of temperature or voltage fluctuation in the unit. If the magnitude of the PM voltage pulses is within the upper operating range, the comparator 240 will generate a logic "0" signal which is inverted by the NAND 256 to clock the flip flop 254 and generate a logic "1" signal at the input 257-1. When the output 240-3 returns to logic "1", the NAND 257 generates a logic "0" pulse on the line 193. This pulse is inverted by the NAND 253 to reset the flip flop 254 and disable the NAND 257 with the logic "0" signal at the output 254-5. If the magnitude of the PM pulses is lower than the magnitude of the signal at the input 240-1, the NAND 257 will generate a continuous logic "1" signal on a line 193. If the magnitude of the PM pulses is greater than the voltage at the input 239-1, the comparator 239 will generate a logic "0" pulse which is inverted by the NAND 253 to reset the flip flop 254. Thus, the output 254-5 is returned to logic "0" before the input 257-2 returns to logic "1" and a continuous logic "1" will be generated on a line 193.

Figure 6:
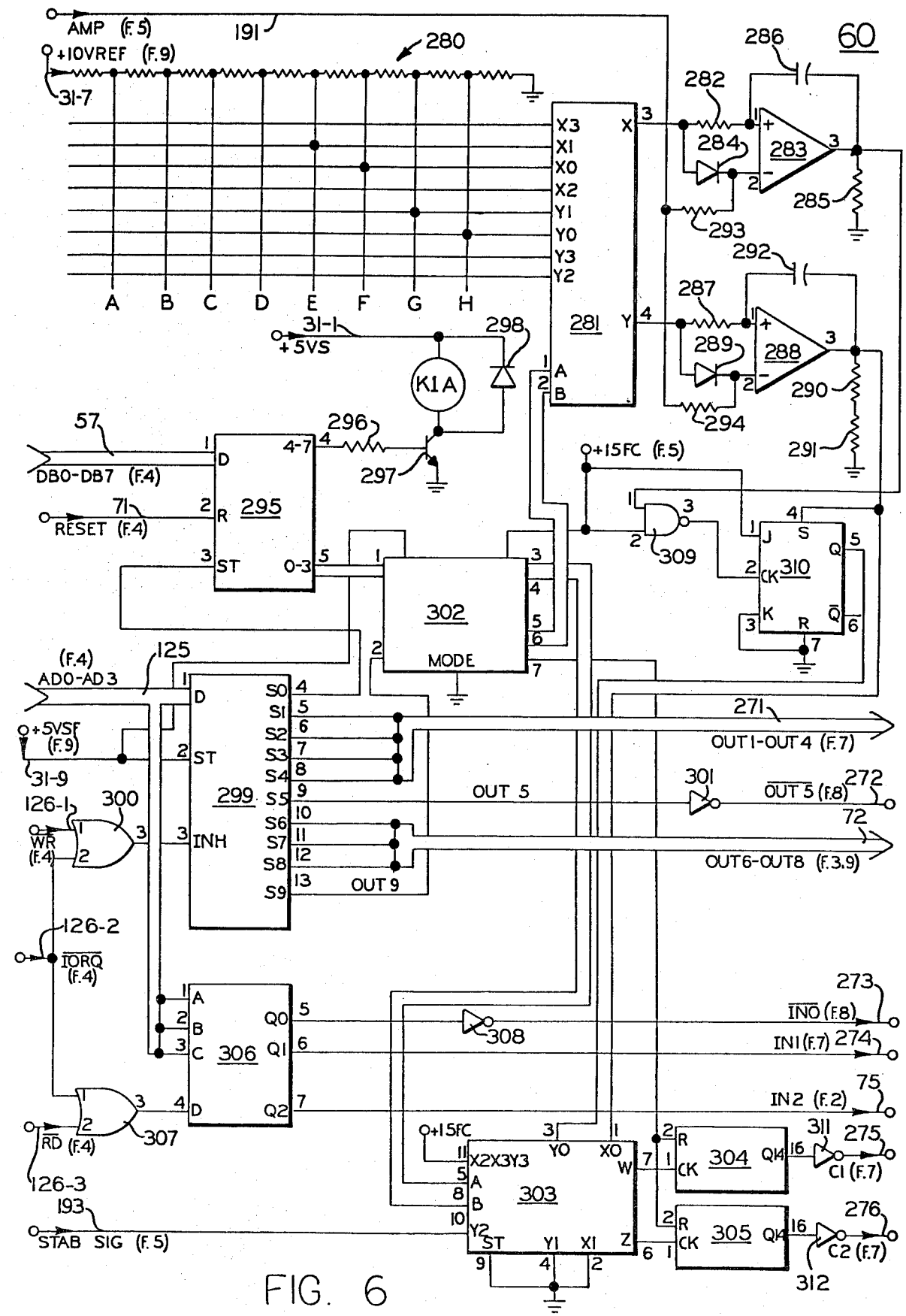
FIGS. 6 and 7 are schematic diagrams of circuitry associated with the pulse amplifier shown in FIG. 5.

There is shown in FIG. 6 a portion of the circuitry associated with the pulse amplifier 60 of FIG. 2. Inputs to the circuits are the AMP signal line 191, the +10VREF power supply line 31-7, the +5VS power supply line 31-1, the +15FC power supply from FIG. 5, the data bus 57, the RESET line 71, the +5VSF power supply from FIG. 3, the AD0-AD3 address signals on the bus 125, the WR line 126-1, the $\overline{IORQ}$ line 126-2, the $\overline{RD}$ line 126-3, and the STAB SIG line 193. Outputs from the circuit are the OUT1-OUT4 signal bus 271, the $\overline{OUT5}$ signal line 272, the OUT6-OUT8 signal bus 72, the $\overline{IN0}$ signal line 273, the IN1 signal line 274, the IN2 signal line 75, a C1 signal line 275, and a C2 signal line 276.

The power supply line 31-7 is connected to the circuit ground potential through a plurality of resistors 280 defining a voltage divider. The junctions of the resistors, designated as A through H, can be connected to X and Y inputs of a dual four channel analog multiplexer 281. As shown, the junction E is connected to the input X1, the junction F is connected to the input X0, the junction G is connected to the Y1 input, and the junction H is connected to the Y0 input. The X input signals to the multiplexer are generated at an X output 218-3 which is connected through a resistor 282 to a non-inverting input 283-1 of a differential voltage comparator 283. The output 281-3 is also connected to an anode of a diode 284 having a cathode connected to an inverting input 283-2 of the comparator 283. The comparator 283 has an output 283-3 which is connected through a resistor 285 to the circuit ground potential and connected through a capacitor 286 to the input 283-1. The Y input signals are generated at a Y output 281-4 which is connected through a resistor 287 to a non-inverting input 288-1 of a differential voltage comparator 288. The output 281-4 is also connected to an anode of a diode 289 having a cathode connected to an inverting input 288-2 of the comparator 288. The comparator 288 has an output 288-3 which is connected to the circuit ground potential through a pair of series connected resistors 290 and 291 and to the non-inverting input 288-1 through a capacitor 292. The AMP line 191 is connected to the inverting input 283-2 through a resistor 293 and to the inverting input 288-2 through a resistor 294.

The data bus 57 is connected to a plurality of data inputs 295-1 of a dual four bit latch 295. The RESET line 71 is connected to a reset input 295-2 of the latch 295. An output 295-4 is connected to a relay driver circuit which is representative of four such circuits, one for each of the DB4-DB7 data bits. The output 295-4 is connected through a resistor 296 to a base of an NPN transistor 297. The transistor 297 has as emitter connected to the circuit ground potential and a collector connected to the power supply line 31-1 through a K1A relay coil. A diode 298 has an anode connected to the collector of the transistor 297 and a cathode connected to the line 31-1.

The address lines 125 are connected to data inputs 299-1 of a four to sixteen line decoder/latch 299. The +5VSF power supply voltage from FIG. 3 is connected to a strobe input 299-2. The $\overline{WR}$ line 126-1 is connected to an input 300-1 of an OR gate 300 having an input 300-2 connected to the IORQ line 126-2 and an output 300-3 connected to an INH inhibit input 299-3. The decoder/latch 299 has ten outputs S0 to S9. An OUT0 signal is generated at an S0 output 299-4 which is connected to a strobe input 295-3 of the latch 295. Output signals OUT1-OUT4 are generated at outputs 299-5 through 299-8 which are connected to the bus 271. An $\overline{OUT5}$ signal is generated at an output 299-9 which is connected to the line 272 through an inverter 301. Output signals OUT6-OUT8 are generated at outputs 299-10 through 299-12 which are connected to the bus 72. An output signal OUT9 is generated at the output 299-13 which is connected to an input 302-2 of a level shifter 302. Four outputs 295-5 of the latch 295 corresponding to the data bits DB0-DB3 are connected to four inputs 302-1 of the level shifter 302. Outputs 302-3 and 302-4, representing the DB1 and DB0 data bits respectively, are connected to an A input 303-5 and a B input 303-8 of a dual four-channel data selector 303. Outputs 302-5 and 302-6, corresponding to the DB2 and the DB3 data bits, are connected to an A input 281-1 and a B input 281-2 of the multiplexer. The OUT9 signal at the input 302-2 is generated at an output 302-7 which is connected to a pair of reset inputs 304-2 and 305-2 of a pair of fourteen-bit bin counters 304 and 305, respectively.

The AD0-AD2 lines of the bus 125 are connected to inputs 306-1 through 306-3 respectively of a BCD to decimal decoder 306. The line 126-2 is connected to an input 307-1 of an OR gate 307 having an input 307-2 connected to the line 126-3 and an output 307-3 connected to an input 306-4 of the decoder 306. The signals at the inputs 306-1 through 306-4 are a binary coded number which is decoded to generate a decimal output signal from one of three outputs 306-5 through 306-7. The output 306-5 is connected through an inverter 308 to the line 273, the output 306-6 is connected to the line 274, and the output 306-7 is connected to the line 75.

The output 283-3 of the comparator 283 is connected to an input 309-1 of a NAND gate 309. The gate 309 has an input 309-2 connected to the +15FC power supply of FIG. 5 and an output 309-3 connected to a clock input 310-2 of a J-K type flip flop 310. The flip flop 310 has a J input 310-1 connected to the 30 15FC power supply and a K input 310-3 connected to a set input 310-7. The output 288-3 of the comparator 288 is connected to a set input 310-4 of the flip flop 310.

The output 288-3 of the comparator 288 is connected to an X0 input 303-1 of the data selector 303. A non-inverting output 310-5 of the flip flop 310 is connected to a Y0 input 303-3 of the data selector 303. An input 303-11, representing the X2, X3, and Y3 inputs is connected to the +15FC power supply. A Y2 input 303-10 is connected to the line 193. A strobe input 303-9, a Y1 input 303-4, and an X1 input 303-2 are connected to the circuit ground potential. A W output 303-7 is connected to a clock input 304-1 of the counter 304. A Z output 303-6 is connected to a clock input 303-1 of the counter 305. The counter 304 has a Q14 output 304-16 connected to the line 275 through an inverter 311 and the counter 305 has a Q14 output 305-16 connected to the line 276 through an inverter 312.

The CPU generates data bits on the bus 57 and address bits on the bus 125 to strobe the latch 295. The latch responds to the data bits by driving the selected relay coil(s) for selecting the gain of the amplifier shown in FIG. 5 and for selecting the reference voltage levels for the comparators 283 and 288 through the multiplexer 281. If the amplitude of the AMP pulses on the line 191 is less than the magnitude of the lower reference voltage, the inputs 303-1 and 303-3 of the data selector 303 will both be at logic "1". If the magnitude of the pulses is between the upper and lower reference voltage levels, the comparator 288 will generate logic "0" pulses to the input 303-1 which pulses appear at the Z output 303-6 and are counted by the counter 305. If the magnitude of the AMP pulses exceeds the upper reference voltage, the comparator 283 will generate logic "0" pulses which are inverted by the NAND 309 to clock the flip flop 310. The flip flop 310 generates a logic "0" pulse to the Y0 input 303-3 which pulses appear at the W output 303-7 and are counted by the counter 304. The comparator 288 also generates a logic "1" pulse which sets the flip flop 310. Thus, the signals C1 on the line 275 and C2 on the line 276 represent the number of AMP pulses with magnitudes exceeding the upper reference voltage level and the lower reference voltage level respectively.

The CPU also utilizes the decoder/latch 299 to generate output signals OUT1-OUT8 for the operation of the system. The CPU utilizes the decoder 306 to generate control signals for various inputs to the circuitry. The data selector 303 controls the counting of the upper and lower level AMP signal pulses by the counters 304 and 305, monitors the STAB SIG signal on the line 193, and permits the counters 304 and 305 to be counted down to zero.

Figure 7:
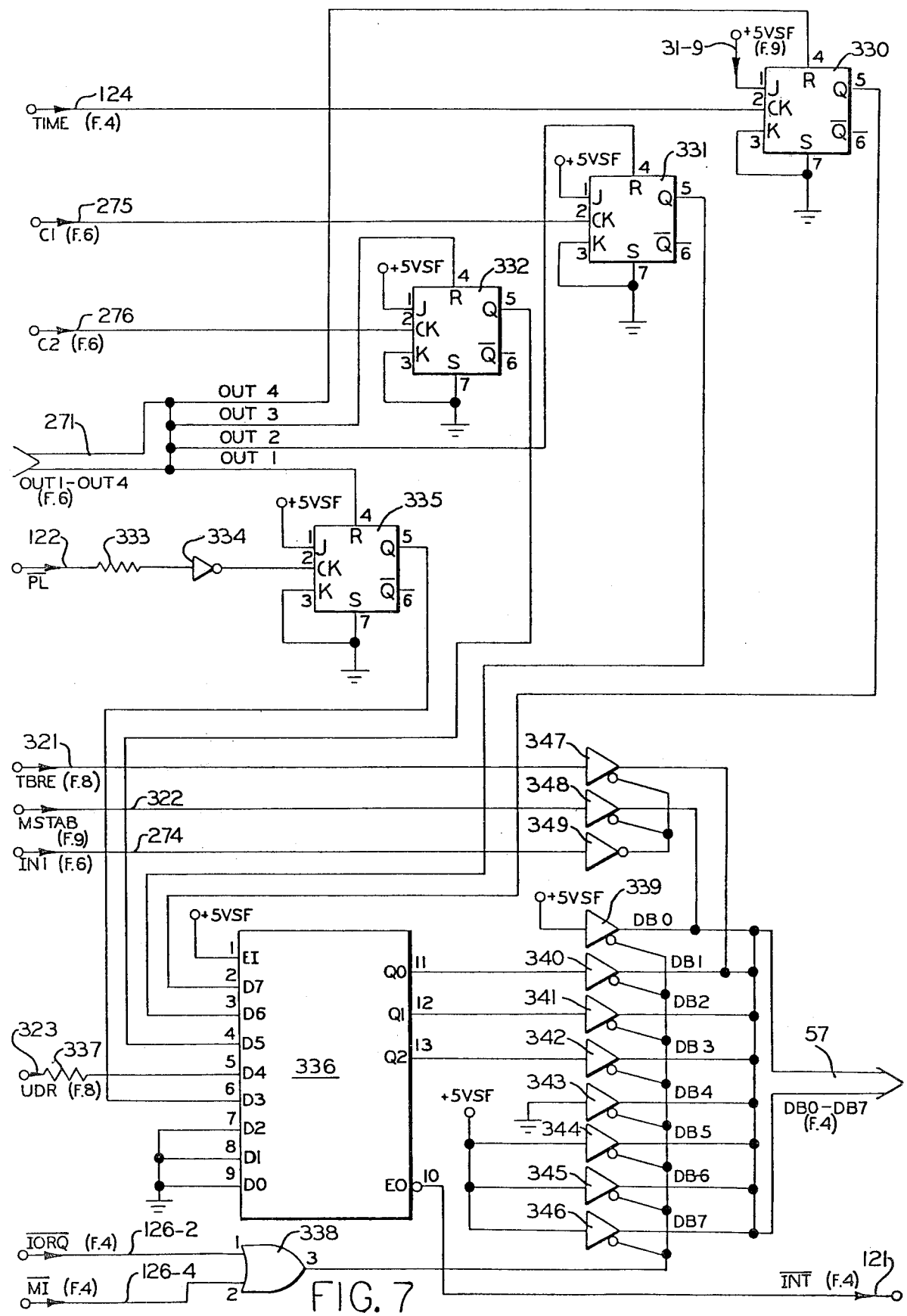

There is shown in FIG. 7 another portion of the circuitry associated with the pulse amplifier. Inputs to the circuitry are the TIME line 124, the C1 line 275, the C2 line 276, the OUT1-OUT4 bus 271, the $\overline{PL}$ line 122, a TBRE line 321, a $\overline{MSTA}$ line 322, the $\overline{IN1}$ line 274, a UDR line 323, the $\overline{INT}$ line 121, the $\overline{IORQ}$ line 126-2, the $\overline{M1}$ line 126-4 and the +5VSF power supply voltage from FIG. 3. Outputs from the circuit of FIG. 7 are the DB0-DB7 data bits on the data bus 57.

The line 124 is connected to a clock input 330-2 of a J-K flip flop 330. The flip flop 330 has a J input 330-1 connected to the +5VSF power supply and a K input 330-3 connected to the circuit ground potential. The OUT4 signal line of the bus 271 is connected to a reset input 330-4 of the flip flop 330.

The line 275 is connected to a clock input 331-2 of a J-K flip flop 331. The flip flop 331 has a J input 331-1 connected to the +5VSF power supply and a K input 331-3 connected to the circuit ground potential. The OUT2 signal line of the bus 271 is connected to a reset input 331-4.

The line 276 is connected to a clock input 332-2 of a J-K flip flop 332. The flip flop has a J input 332-1 connected to the 30 5VSF power supply and a K input 332-3 connected to the circuit ground potential. The OUT3 signal line of the bus 271 is connected to a reset input 332-4.

The line 122 is connected through a resistor 333 and an inverter 334 to a clock input 335-2 of a J-K flip flop 335. A J input 335-1 is connected to the +5VSF power supply and a K input 335-3 is connected to the circuit ground potential. The OUT1 line of the bus 271 is connected to a reset input 335-4.

An eight-bit priority encoder 336 has an enable input 336-1 connected to the +5VSF power supply to enable a plurality of data inputs 336-2 through 336-9. A D7 input 336-2 is connected to a non-inverting output 330-5 of the flip flop 330. A D6 input 336-3, a D5 input 336-4, and a D3 input 336-3 are connected to non-inverting outputs 331-5, 332-5, and 335-5, respectively. A D4 input is connected to the line 323 through a resistor 337. A D2 input 336-7, a D1 input 336-8, and a D0 input 336-9 are all connected to the circuit ground potential. The line 121 is connected to an enable input 336-10.

The line 126-2 is connected to an input 338-1 and the line 126-4 is connected to an input 338-2 of an OR gate 338 having an output 338-3 connected to an enable input of each of a plurality of tri-state gates 339 through 346. The gate 339 has an input connected to the +5VSF power supply and an output connected to the data bus 57 to generate a logic "1" DB0 signal when enabled. A Q0 output 336-11 of the encoder 336 is connected to an input of the gate 340 which has an output connected to the bus 57 to generate the DB-1 signal when enabled. A Q1 output 336-12 is connected to an input of the gate 341 which has an output connected to the bus 57 to generate the DB2 signal when enabled. A Q2 output 336-13 is connected to an input of the gate 342 which has an output connected to the bus 57 to generate the DB3 signal when enabled. The gate 343 has an input connected to the circuit ground potential and an output connected to the bus 57 to generate a logic "0" DB4 signal when enabled. The gates 344, 345 and 346 each have an input connected to the +5VSF power supply. The gate 344 has an output connected to the bus 57 to generate the DB5 signal when enabled, the gate 345 has an output connected to the bus 57 to generate the DB6 signal when enabled, and the gate 346 has an output connected to the bus 57 to generate the DB7 signal when enabled.

The line 321 is connected to an input of a tri-state gate 347 which is an output connected to the bus 57 to generate the DB1 signal when enabled. The line 322 is connected to an input of a tri-state gate 348 which has an output connected to the data bus 57 to generate the DB0 signal when enabled. The line 274 is connected through an inverter 349 to the enable inputs of the gates 347 and 348.

The signals TIME, C1, C2, $\overline{PL}$, and UDR are all interrupts to the system. The encoder 336 will generate, at the outputs 336-11 through 336-13, a binary coded signal representing the highest order input which has received a signal, with input 336-2 being the highest order and input 336-9 being the lowest order. A signal on one of the inputs generates the $\overline{INT}$ signal at the output 336-10 on the line 121 to the CPU. The CPU then generates the signals on the lines 126-2 and 126-4 to enable the tri-state gates and place the three data bits representing the highest order interrupt being generated onto the data bus 57. The CPU can then read the code for the interrupt to determine what device requires servicing.

Figure 8:
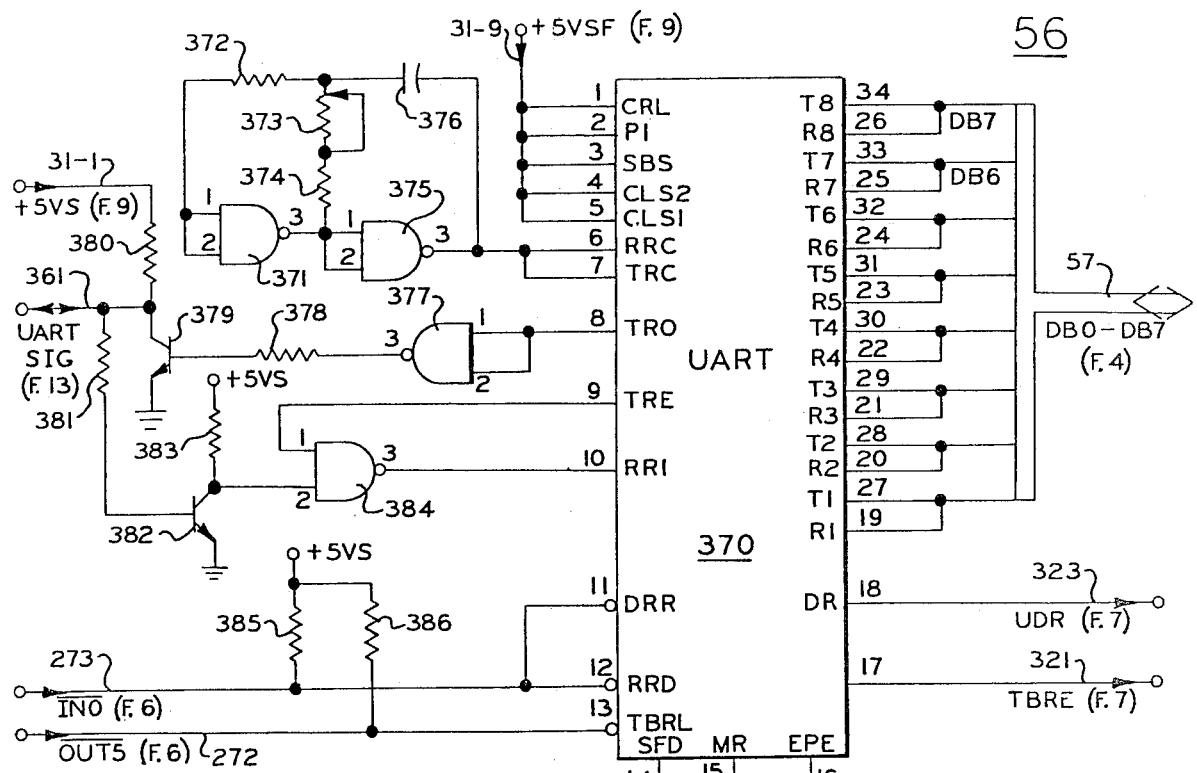
FIG. 8 is a schematic diagram of the UART and a portion of the main power supply shown in FIG. 2.
Figure 8:
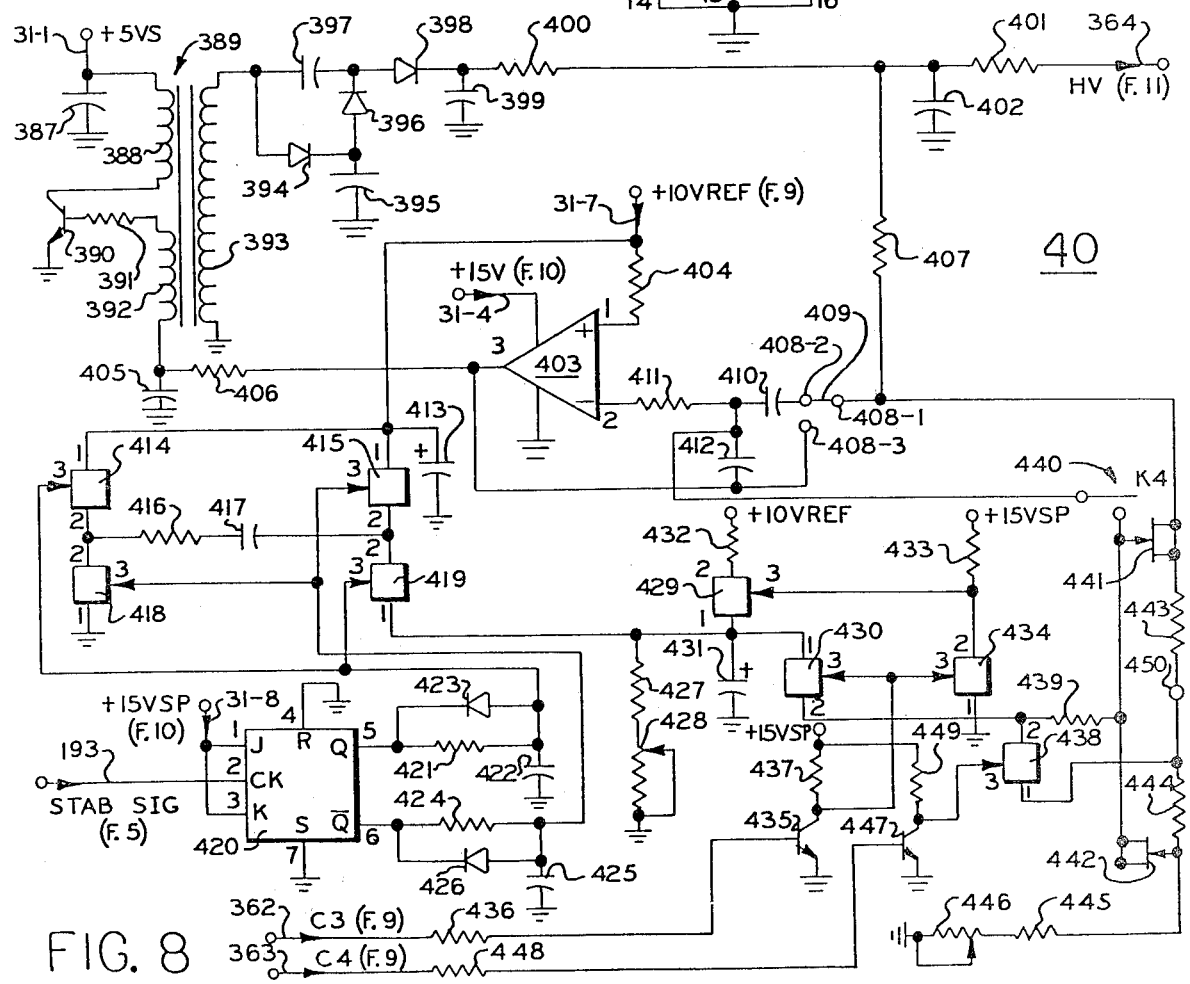

There is shown in FIG. 8 the UART 56 and a portion of the main power supply 40. Inputs to the UART are the +5VSF power supply line 31-9, the +5VS power supply line 31-1, a bidirectional UART SIG line 361, the $\overline{IN0}$ signal line 273, and the $\overline{OUT5}$ line 272. Outputs from the UART are the bidirectional data bus 57, the UDR line 323, and the TBRE line 321. Inputs to the main power supply are the 30 5VS power supply line 31-1, the +15V power supply line 31-4, the +10VREF power supply line 31-7, a +15VSP power supply line 31-8, the STAB SIG signal line 193, a C3 control signal line 362, and a C4 control signal line 363. The output from the main power supply is a HV signal line 364.

The power supply line 31-9 is connected to inputs 370-1 through 370-5 of a model IM6402A UART 370. A NAND gate 371 has a pair of inputs 371-1 and 371-2 connected to an output 371-3 through a series connected resistor 372, potentiometer 373, and resistor 374. The output 371-3 is connected to a pair of inputs 375-1 and 375-2 of a NAND 375. The NAND 375 has an output 375-3 connected to the junction of the resistor 372 and the potentio meter 373 through a capacitor 376. The output 375-3 is also connected to a pair of inputs 370-6 and 370-7 of the UART 370.

An output 370-8 is connected to a pair of inputs 377-1 and 377-2 of a NAND 377. The NAND 377 has an output 377-3 connected through a resistor 378 to a base of an NPN transistor 379. The transistor 379 has an emitter connected to the circuit ground potential and a collector connected to the power supply line 31-1 through a resistor 380. The collector of the transistor 379 is also connected to the UART SIG line 361 and through a resistor 381 to a base of an NPN transistor 382. The transistor 382 has an emitter connected to the circuit ground potential and a collector connected to the +5VS power supply through a resistor 383. The collector is also connected to an input 384-2 of a NAND gate 384 having another input 384-1 connected to an output 370-9 of the UART and an output 384-3 connected to an input 370-10 of the UART.

The $\overline{IN0}$ line 273 is connected to the +5VS power supply through a resistor 385 and to a pair of inputs 370-11 and 370-12 of the UART. The $\overline{OUT5}$ signal line 272 is connected to the +5VS power supply though a resistor 386 and to an input 370-13 of the UART. The UART 370 has inputs 370-14, 370-15, and 370-16 connected to the circuit ground potential.

The line 321 is connected to an output 370-17 and the line 323 is connected to an output 370-18 of the UART. The UART also has a plurality of transmit and receive terminals which are connected to the data bus 57. Receive terminals 370-19 through 370-26 are connected to the data bus 57 to generate the data bits DB0 through DB7, respectively. Transmit terminals 370-27 through 370-34 are connected to the data bus 57 to input the data bits DB0 through DB7, respectively.

The UART 370 is utilized to communicate with the probe. The NAND 377 and the transistor 379 are the output signal controls and the transistor 382 and the NAND 384 are the input signal controls for the UART. Signals are transmitted in a serial manner on the UART SIG line 361 to and from the probe under the control of these devices. The NANDs 371 and 375 together with the associated resistors and capacitor form an oscillator which determines the frequency of the transmission and receiving operation of the UART. The $\overline{IN0}$ signal on the line 273 selects the receiving operation and the $\overline{OUT5}$ signal on the line 272 selects the transmitting operation.

The power supply line 31-1 is connected to the circuit ground potential through a capacitor 387 and through a portion 388 of a primary winding of a transformer 389 to a collector of an NPN transistor 390. The transistor 390 has an emitter connected to the circuit ground potential and a base connected through a resistor 391 and a second portion 392 of the primary winding of the transformer 389 through the capacitor 405 to the circuit ground potential. The transformer 389 has a secondary coil 393 having one end connected to the circuit ground potential and the other end connected to an anode of a diode 394. The diode 394 has a cathode connected through a capacitor 395 to the circuit ground potential and to an anode of a diode 396. The diode 396 has a cathode connected to the anode of the diode 394 through a capacitor 397 and to an anode of a diode 398. The diode 398 has a cathode connected to circuit ground potential through a capacitor 399 and to the line 364 through a pair of series connected resistors 400 and 401. The junction of the resistors 400 and 401 is connected to the circuit ground potential through a capacitor 402.

An operational amplifier 403 has a non-inverting input 403-1 connected to the +10VREF power supply through a resistor 404. The amplifier 403 has an output 403-3 connected to the junction of the winding 392 and the capacitor 405 through a resistor 406. The junction of the resistors 400 and 401 is connected through a resistor 407 to a terminal 408-1. The terminal 408-1 is connected to a terminal 408-2 by a jumper 409. The terminal 408-2 is connected through a capacitor 410 and a resistor 411 connected in series to an inverting input 403-2 of the amplifier 403. The junction of the capacitor 410 and the resistor 411 is connected to the output 403-3 through a capacitor 412. The output 403-3 is also connected to a terminal 408-3. When it is desired to manually stabilize the analyzer, the jumper 409 is removed and a jumper is installed between the terminals 408-2 and 408-3.

The power supply line 31-7 is connected to the circuit ground potential through a capacitor 413 and to an input 414-1 and an input 415-1 of a pair of bi-lateral switches 414 and 415, respectively. The switch 414 has an output 414-2 connected through a series connected resistor 416 and a capacitor 417 to an output 415-2 of the switch 415. The output 414-2 is also connected to an output 418-2 of a bi-lateral switch 418 having an input 418-1 connected to the ground circuit ground potential. The output 415-2 is connected to an ouput 419-2 of a bi-lateral switch 419.

The power supply line 38-1 is connected to a J input 420-1 and a K input 420-3 of a J-K flip flop 420. The line 193 is connected to a clock input 420-2 of the flip flop. A non-inverting output 420-5 is connected through a resistor 421 to a control input 414-3 of the switch 414 and a control input 419-3 of the switch 419. The output 420-5 is also connected through the resistor 421 and a series connected capacitor 422 to the circuit ground potential. A diode 423 has an anode connected to the junction of the resistor 421 and the capacitor 422 and a cathode connected to the output 420-5. An inverting output 420-6 is connected through a resistor 424 to a control input 418-3 of the switch 418 and a control input 415-3 of the switch 415. The output 420-6 is connected through a resistor 424 and a series connected capacitor 425 to the circuit ground potential. A diode 426 has an anode connected to the junction of the resistor 424 and the capacitor 425 and a cathode connected to the output 420-6.

An input 419-1 of the switch 419 is connected through a series connected resistor 427 and a potentiometer 428 to the circuit ground potential. The input 419-1 is also connected to an input 429-1 of a bi-lateral switch 429, an input 430 of a bi-lateral switch 430, and the circuit ground potential through a capacitor 431. The switch 429 has an output 429-2 connected to the +10VREF power supply through a resistor 432 and a control input 429-3 connected to the +15VSP power supply through a resistor 433. The control signal input 429-3 is also connected to an output 434-2 of a bi-lateral switch 434. The switch 434 has an input 434-1 connected to the circuit ground potential and a control signal input 434-3 connected to a control signal input 430-3 of the switch 430. The control signal inputs 430-3 and 434-3 are connected to a collector of an NPN transistor 435. The C3 signal line 362 is connected through a resistor 436 to a base of the transistor 435. The transistor 435 has an emitter connected to the circuit ground potential and a collector connected through a resistor 437 to the +15VSP power supply.

The switch 430 has an output 430-2 connected to an output 438-2 of a bi-lateral switch 438. The outputs 430-2 and 438-2 are connected through a resistor 439 to a fixed terminal of a relay controlled switch 440. A movable terminal of the switch 440 is connected to the junction of the capacitor 410 and the resistor 411. The fixed contact of the switch 440 is connected to a gate of an N-channel FET 441 and a source and a drain of an N-channel FET 442. A source and a drain of the FET 441 are connected to the terminal 408-1. An input 438-1 of the switch 438 is connected through a resistor 443 to the source and the drain of the FET 441. The input 438-1 is also connected through a resistor 444 to a gate of the FET 442. The gate of the FET 442 is connected through a series connected resistor 445 and potentiometer 446 to the circuit ground potential. A control signal input 438-3 of the switch 438 is connected to a collector of a NPN transistor 447. The C4 signal line 363 is connected through a resistor 448 to a base of the transistor 447. The transistor 447 has an emitter connected to the ground potential and the collector is connected to the +15VSP power supply through a resistor 449. A terminal 450 is connected between the resistors 443 and 444 and is utilized during the manual stabilization operation as will be discussed below.

The portion of the high power supply circuit 40 shown in FIG. 8 generates the high voltage signal to the probe on the line 364. The STAB SIG signal on the line 193, from the amplifier shown in FIG. 5, is an input to the flip flop 420 which controls a pump circuit supplying a feedback voltage to the high voltage power supply. The pump circuit includes the bi-lateral switches 414, 415, 418, 419, 429, 430, 434 and 438. This pump circuit is described in more detail in U.S. Pat. No. 3,656,000. The output from the pump circuit is an input to the control amplifier 403. The amplifier 403 supplies a voltage to control the amplitude of the oscillation in a feedback circuit from the transistor 390.

The five volt input of the transformer 389 is chopped by the transistor 390 and stepped up by a high voltage tripler which outputs a voltage that can be adjusted between 800 and 2000 volts. This high voltage signal is fed back through the resistors 407, 443, 444, 445, and 446 which form a voltage divider. The voltage is coupled back into the control amplifier 403 through the capacitor 410 and the transistors 441 and 442. The normal feedback path is through the capacitor 410, and the transistors 441 and 442 limit the feedback voltage to a preselected range as adjusted by the potentiometer 446. If the switch 440 is opened and the switch 430 is also opened, the feedback signal is removed and the voltage across the capacitor 410 is maintained constant for approximately five minutes. During this period, interference from the sources is eliminated while the STAB SIG signal is counted by the circuit in FIG. 6.

Figure 9:
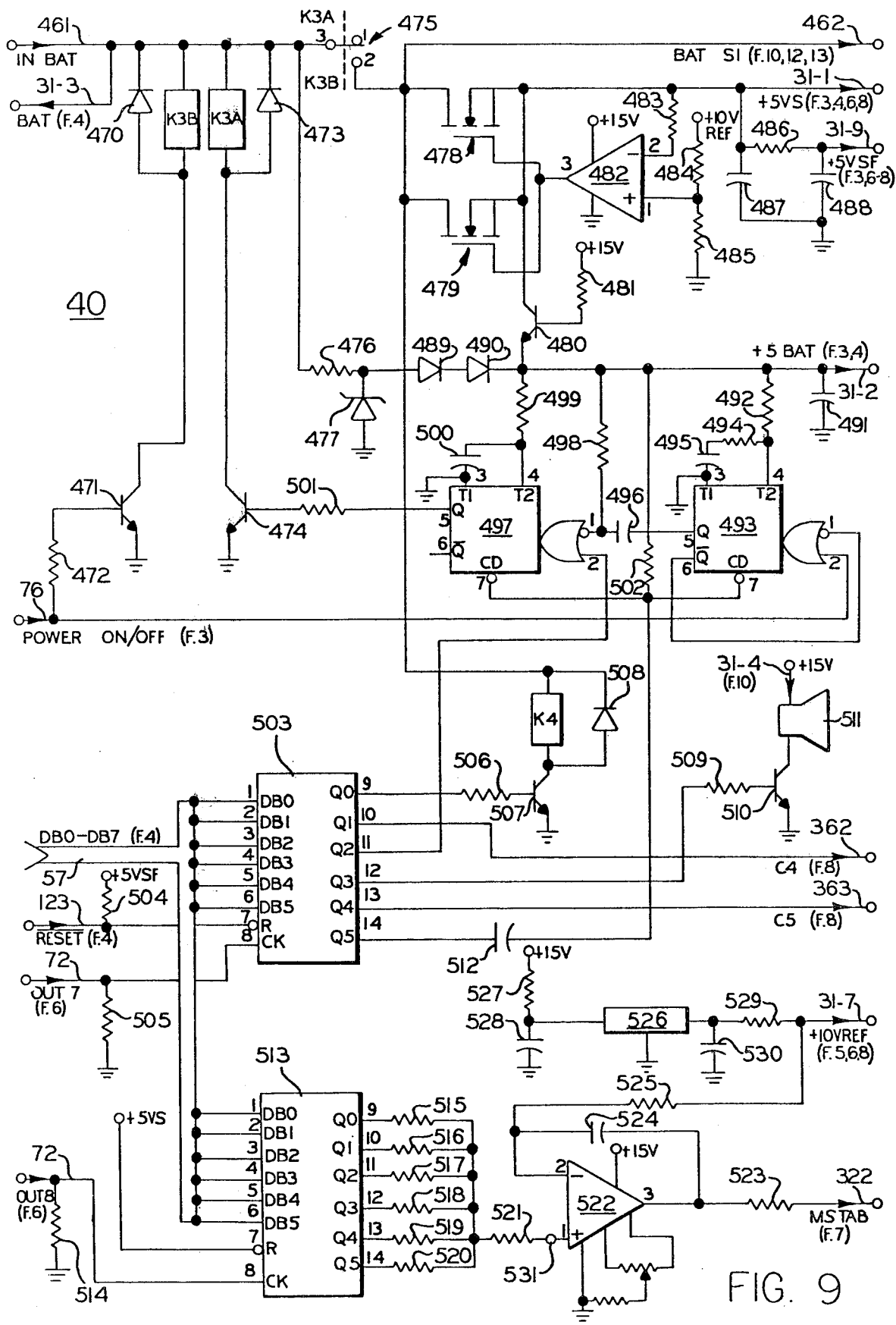
FIGS. 9 and 10 are schematic diagrams of the remainder of the main power supply shown in FIG. 2.

There is shown in FIG. 9 another portion of the main power supply 40. Inputs to the circuit are an IN BAT line 461, the POWER ON/OFF line 76, the data bus 57, the RESET line 123, the OUT7 line 72, the OUT8 line 72, and the +15V power supply line 31-3. Outputs from the circuit are the BAT power supply line 31-3, a BAT S1 power supply line 462, the +5VS power supply line 31-1, the +5VSF power supply line 31-9, the +5BAT power supply line 31-2, the C4 signal line 362, the C5 signal line 363, the +10VREF power supply line 31-7, and the MSTAB signal line 322.

The line 461 is connected to a battery (not shown) for supplying power to all the analyzer circuitry. The line 461 is connected to a cathode of a diode 470 having an anode connected to a collector of a NPN transistor 471. The transistor 471 has an emitter connected to the circuit ground potential and a base connected to the line 76 through a resistor 472. The transistor 474 has an emitter connected to the circuit ground potential and the collector is connected to the line 461 through a K3A relay coil. The line 461 is connected to a cathode of a diode 473 having an anode connected to a collector of an NPN transistor 474. The transistor 474 has an emitter connected to the circuit ground potential and the collector connected to the line 461 through a K3A relay coil. The line 461 is connected to a movable contact 475-3 of the K3 relay, and is connected through a resistor 476 to a cathode of a zener diode 477 having an anode connected to the circuit ground potential.

A fixed contact 475-2 of the K3 relay is connected to the line 462, a drain of an N-channel FET 478, and a drain of an N-channel FET 479. The FET 478 has a source connected to the line 31-1, to a source of the FET 479 and to a collector of an NPN transistor 480. The transistor 480 has a base connected to the +15V power supply through a resistor 481 and an emitter connected to the line 31-2. A gate of each of the FETs is connected to an output 482-3 of an operational amplifier 482. An inverting input 482-2 of the amplifier 482 is connected to the line 31-1 through a resistor 483. A non-inverting input 482-1 is connected to the +10VREF power supply through a resistor 484 and to the circuit ground potential through a resistor 485. The line 31-1 is connected through a resistor 486 to the line 31-9 and to the circuit ground potential through a capacitor 487. The line 31-9 is connected to the circuit ground potential through a capacitor 488.

The cathode of the zener diode 477 is connected to an anode of a diode 489 having a cathode connected to an anode of a diode 490 having a cathode connected to the line 31-2. The line 31-2 is connected to the circuit ground potential through a capacitor 491. The line 31-2 is connected through a resistor 492 to a second timing input 493-4 of a retriggerable/resettable monostable multivibrator 493. The input 493-4 is connected through a resistor 494 and a capacitor 495 connected in series to a first timing input 493-3 which is also connected to the circuit ground potential. An inverting input 493-1 of the multivibrator is connected to the line 76 and a non-inverting input 493-2 is connected to an inverting output 493-6. A non-inverting output 493-5 is connected through a capacitor 496 to an inverting input 497-1 of a retriggerable/resettable monostable multivibrator 497. The input 497-1 is also connected to the line 31-2 through a resistor 498. The input 31-2 is connected to a second timing input 497-4 through a resistor 499. The timing input 497-4 is connected to a first timing input 497-3 through a capacitor 500. The input 497-3 is also conneted to the circuit ground potential. A non-inverting output 497-5 is connected through a resistor 501 to a base of the transistor 474. The line 31-2 is connected through a resistor 502 to a clear input 493-7 and a clear input 497-7.

The data bus 57 is connected to inputs 503-1 through 503-6 of a hex D-type flip flop 503. The line 123 is connected to a reset input 503-7 and to the +5VSF power supply through a resistor 504. The OUT7 line 72 is connected to a clock input 503-8 and the circuit ground potential through a resistor 505. A Q0 output 503-9 is connected through a resistor 506 to a base of an NPN transistor 507. The transistor 507 has an emitter connected to the circuit ground potential and a collector connected to an anode of a diode 508 having a cathode connected to the K3 relay contact 475-2. A K4 relay coil is connected across the diode 508 and is associated with the switch 440 of FIG. 8. A Q1 output 503-10 is connected to the line 362. A Q2 output 503-11 is connected to a non-inverting input 497-2 of the multivibrator 497. A Q3 output 503-12 is connected through a resistor 509 to a base of an NPN transistor 510. The transistor 510 has an emitter connected to the circuit ground potential and a collector connected through a coil of a speaker 511 to the power supply line 31-4. A Q4 output 503-13 is connected to the line 363. A Q4 output 503-14 is connected through a capacitor 512 to the clear inputs 493-7 and 497-7 of the multivibrators.

The data bus 57 is connected to data inputs 513-1 through 513-6 of a hex D-type flip flop 513. A reset input 513-7 is connected to the +5VF power supply and a clock supply input 513-8 is connected to the OUT8 signal line 72 which is also connected through a resistor 514 to the circuit ground potential. The hex flip flop 513 has outputs 513-9 through 513-14 connected to individual resistors 515 through 520. The resistors 515 through 520 are connected in parallel through a resistor 521 to a non-inverting input 522-1 of an operational amplifier 522. The amplifier 522 has an output 522-3 connected through a resistor 523 to the line 322 and an inverting input 522-1 connected through a capacitor 524 to the output 522-3 and through a resistor 525 to the line 31-7. An input of a voltage regulator circuit 526 is connected to the +15V power supply through a resistor 527 and to the circuit ground potential through a capacitor 528. An output of the voltage regulator 526 is connected to the line 31-7 through a resistor 529 and to the circuit ground potential through a capacitor 530.

A terminal 531 is connected to the non-inverting input 522-1 of the amplifier 522. A jumper is connected between the terminal 531 and the terminal 450 in FIG. 8 when it is desired to manually stabilize the circuit. The CPU generates data bits which are latched into the flip flop 513 of the OUT8 signal on the line 72. These data bits select one or more of the resistors 515 through 520 to generate a predetermined voltage to the amplifier 522. The amplifier 522 generates the MSTAB signal to the circuit of FIG. 7 for the manual stabilization operation. During this time, the pump circuit of FIG. 8 is disabled. The manual stabilization operation is not utilized when the analyzer is to analyze metal.

The flip flop 503 functions as a latch for the K4 relay, the C4 and the C5 control signals to the pump circuit, the control signal for the speaker 513 which generates an audible output when the shutters on the sources have been opened and each time a keyboard key is depressed, and the reset control for the multivibrators 493 and 497.

The battery voltage on the line 461 is continuously available on the output line 31-2 to enable the keyboard encoder of FIG. 3 and the RAMs of FIG. 4. Thus, even though the analyzer has been turned off, no information will be lost from the memory. When the power is turned on, a signal on the line 76 turns on the transistor 471 and current flows through the relay coil K3B to close the contacts 475-2 and 475-3. Power is now supplied to the output lines 31-1, 31-9 and 462. The transistor 480 regulates the voltage on the line 31-2.

The power on signal sets the multivibrator 493. The multivibrators 493 and 497 are connected in series to generate a thirty second delay pulse to the transistor 474. If the CPU does not reset the monostable multivibrators through the output 503-14 before the multivibrator 497 times out, the transistor 474 will be turned on to energize the coil K3A which switches the contact 475-3 to the contact 475-1 and turns off the battery powered system.

Figure 10:
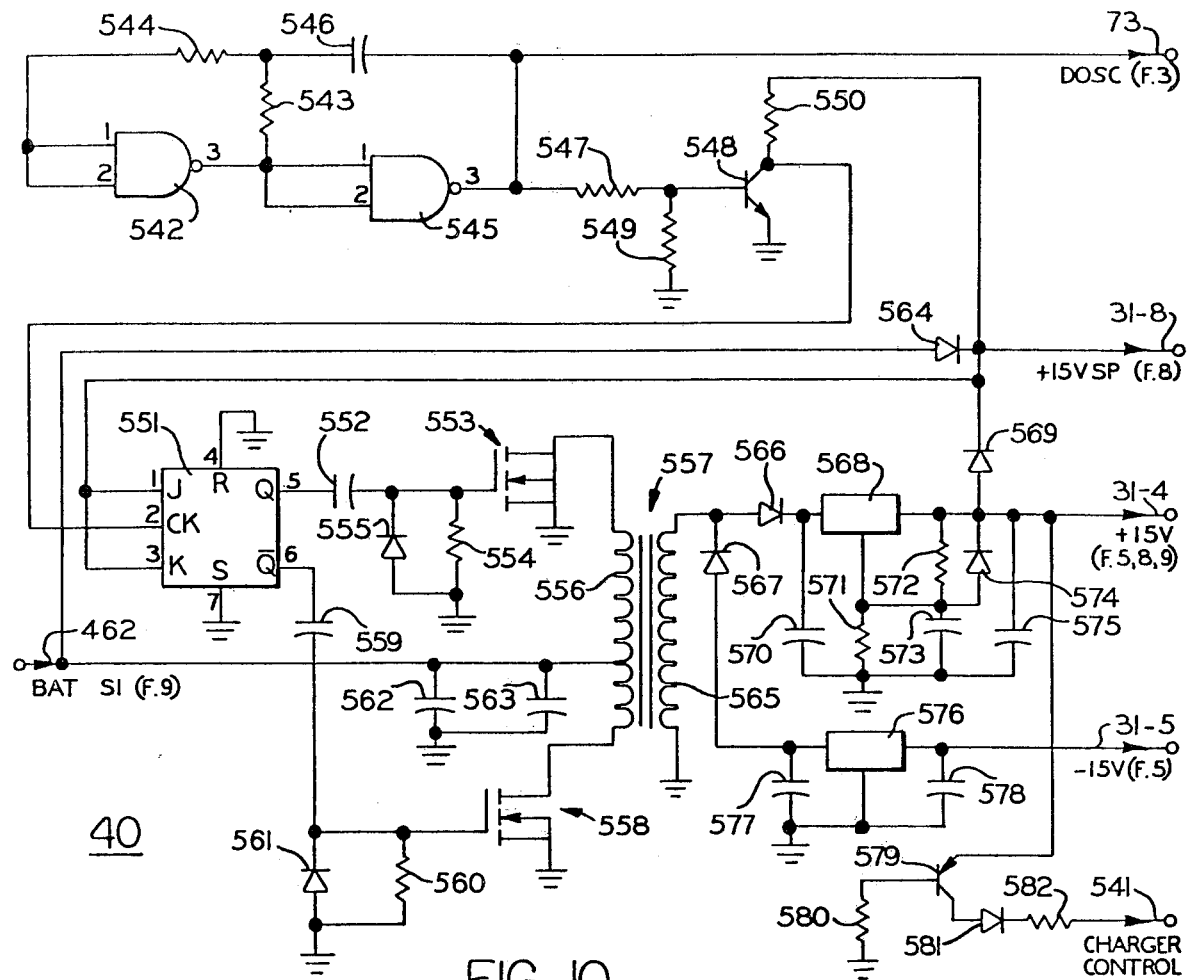

There is shown in FIG. 10 a final portion of the main power supply 40. An input to the circuit is the BAT S1 line 462. Outputs from the circuit are the DOSC line 73, the +15VSP power supply line 31-8, the +15V power supply line 31-4, the −15V power supply line 31-5, and a charger control line 541. A NAND gate 542 has an output 542-3 connected through a pair of series connected resistors 543 and 544 to a pair of inputs 542-1 and 542-2. The output 542-3 is also connected to a pair of inputs 545-1 and 545-2 of a NAND 545. The NAND 545 has an output 545-3 connected to the line 73 and to the junction of the resistors 543 and 544 through a capacitor 546. The output 545-3 is connected through a resistor 547 to a base of an NPN transistor 548. The transistor 548 has an emitter connected to the circuit ground potential. 549. The transistor 548 has a collector connected to the line 31-8 through a resistor 550.

The collector of the transistor 548 is connected to a clock input 551-2 of a J-K flip flop 551. The flip flop 551 has a J input 551-1 and a K input 551-3 connected to the power supply line 31-8. A non-inverting output 551-5 is connected through a capacitor 552 to a gate of a MOSFET 553. The gate of the MOSFET 553 is connected to the circuit ground potential through a resistor 554 and a diode 555 has an anode connected to the circuit ground potential and a cathode connected to the MOSFET 553. A source of the MOSFET 553 is connected to the circuit ground potential and a drain is connected to one end of a primary winding 556 of the transformer 557. The other end of the primary winding 556 is connected to a drain of a MOSFET 558 having a source connected to the circuit ground potential. An inverting output 551-6 of the flip flop 551 is connected through a capacitor 559 to a gate of the MOSFET 558. The gate of the MOSFET 558 is also connected through a resistor 560 to the circuit ground potential and a diode 561 has an anode connected to the circuit ground potential and a cathode connected to the gate of the MOSFET 558. The line 462 is connected to a center tap on the primary winding 556 and to the circuit ground potential through a pair of parallel connected capacitors 562 and 563. The line 462 is also connected to an anode of a diode 564 having a cathode connected to the line 31-8.

One end of a secondary winding 565 of the transformer 557 is connected to the circuit ground potential and the other end is connected to an anode of a diode 566 and a cathode of a diode 567. The diode 566 has a cathode connected to an input of a voltage regulator circuit 568. The voltage regulator 568 has an output connected to the line 31-4 and to an anode of a diode 569 having a cathode connected to the line 31-8. The input of the voltage regulator 568 is connected through a capacitor 570 to the circuit ground potential. A ground reference terminal of the voltage regulator 568 is connected to the circuit ground potential through a resistor 571. The output terminal of the voltage regulator 568 is also connected to the circuit ground potential through a series connected resistor 572 and capacitor 573. A diode 574 has an anode connected to the junction of the resistor 572 and the capacitor 573 and a cathode connected to the line 31-4. A capacitor 575 is connected between the line 31-4 and the circuit ground potential.

The diode 567 has an anode connected to an input of a voltage regulator circuit 576 and to the circuit ground potential through a capacitor 577. An output of the voltage regulator 576 is connected to the line 31-5 and to the circuit ground potential through a capacitor 578. A ground reference terminal of the voltage regulator 576 is connected to the circuit ground potential.

The line 31-4 is connected to an emitter of a PNP transistor 579. The transistor 579 has a base connected to the circuit ground potential through a resistor 580 and a collector connected to an anode of a diode 581. A cathode of the diode 581 is connected to the line 541 through a resistor 582.

The circuit shown in FIG. 10 includes a low voltage DC-to-DC converter. The NANDS 542 and 545, the resistors 543 and 544, and the capacitor 546 function as an RC oscillator which generates a pulse train which is amplified by the transistor 548. The amplified pulse train from the transistor 548 is an input at the clock input 551-2 of the flip flop 551. The flip flop controls the pair of MOSFETs 553 and 558 to chop the BAT S1 battery voltage at the primary winding 556 of the transformer 557. The transformer 557 generates a positive potential output voltage and a negative potential output voltage. The regulator 568 regulates the positive potential output voltage to generate the +15V power supply voltage on the line 31-4. The regulator 576 regulates the negative potential output voltage to generate the −15V power supply voltage on the line 31-5. The transistor 579 and the diode 581 function as a control when the apparatus is plugged into a power source which will charge the internal battery. The transistor and diode generate the Charger Control signal to reduce the charging current such that the internal battery is not overcharged.

Figure 11:
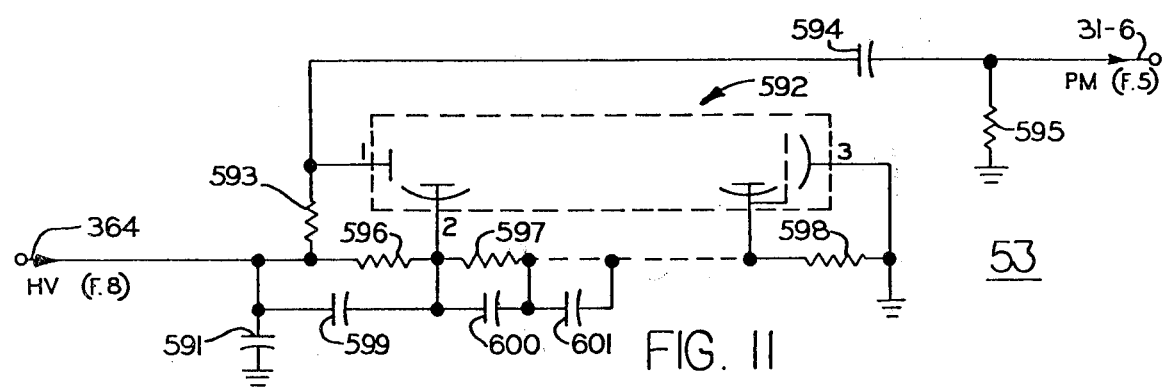
FIG. 11 is a schematic diagram of the detector shown in FIG. 2.

There is shown in FIG. 11 a circuit schematic for the detector 53 of FIG. 2. An input to the circuit is the HV signal on the line 364 and an output from the circuit is the PM signal on the line 31-6.

The line 364 is connected to an anode 592-1 of a photomultiplier tube 592 through a resistor 593. The anode 592-1 is connected to the line 31-6 through a capacitor 594 and the line 31-6 is connected to the circuit ground potential through a resistor 595.

The line 364 is connected to a plurality of dynodes through series connected resistors including resistors 596, 597 and 598. For example, a dynode 592-2 is connected to the junction of the resistors 596 and 597. Electrons emitted from a photo cathode 592-3 are directed from dynode to dynode where they produce many secondary electrons thereby amplifying the signal. A capacitor 599 is connected between the line 364 and the junction of the resistors 596 and 597. A capacitor 600 is connected across the resistor 597 and a capacitor 601 is connected across the next resistor (not shown) in the series of resistors.

The photomultiplier tube 592 has a sodium iodide crystal (not shown) which is excited by the X-rays from the source. The crystal produces light which strikes the photo cathode and generates electrons which are amplified and collected at the anode. Thus, the light is multiplied many times to generate the PM signal on the line 31-6.

Figure 12:
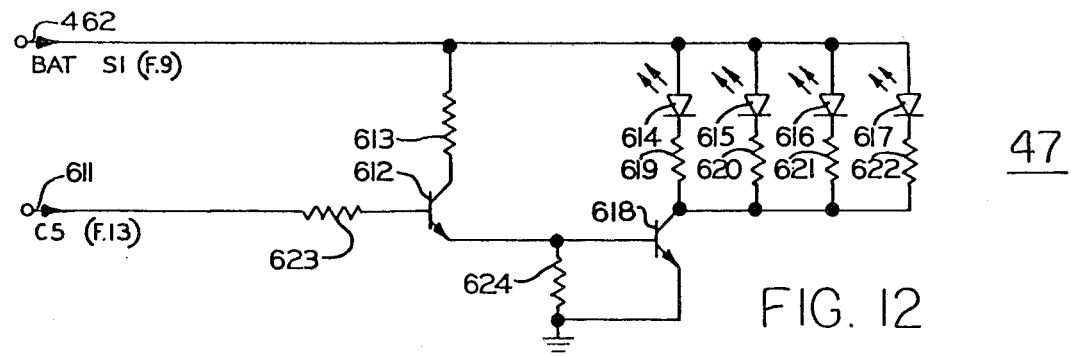
FIG. 12 is a schematic diagram of the filter position transmitter included in the probe control shown in FIG. 2.

There is shown in FIG. 12 a schematic diagram of the filter position transmitter included in the probe control 47 of FIG. 2. Inputs to the circuit are the BAT S1 signal line 462 and C5 control signal line 611. Outputs from the circuit are light generated by a plurality of photodiodes. The line 462 is connected to a collector of an NPN transistor 612 through a resistor 613. The line 462 is also connected to an anode of each of a plurality of light emitting diodes (LED) 614, 615, 616 and 617. The LED 614 has a cathode connected to a collector of an NPN transistor 618 through a resistor 619. The LED 615 has a cathode connected to the collector through a resistor 620, the LED 616 has a cathode connected to the collector through a resistor 621, and the LED 617 has a cathode connected to the collector through a resistor 622. The line 611 is connected to the base of the transistor 612 through a resistor 622. The transistor 612 has an emitter connected to the circuit ground potential through a resistor 624, and to a base of the transistor 618. The transistor 618 has an emitter connected to the circuit ground potential.

When the C5 control signal in generated on the line 611, the transistor 612 is turned on to turn on the transistor 618 and enable the LEDs 614 through 617. The LEDs 614 through 617 generate light to a filter position receiver shown in FIG. 13.

Figure 13:
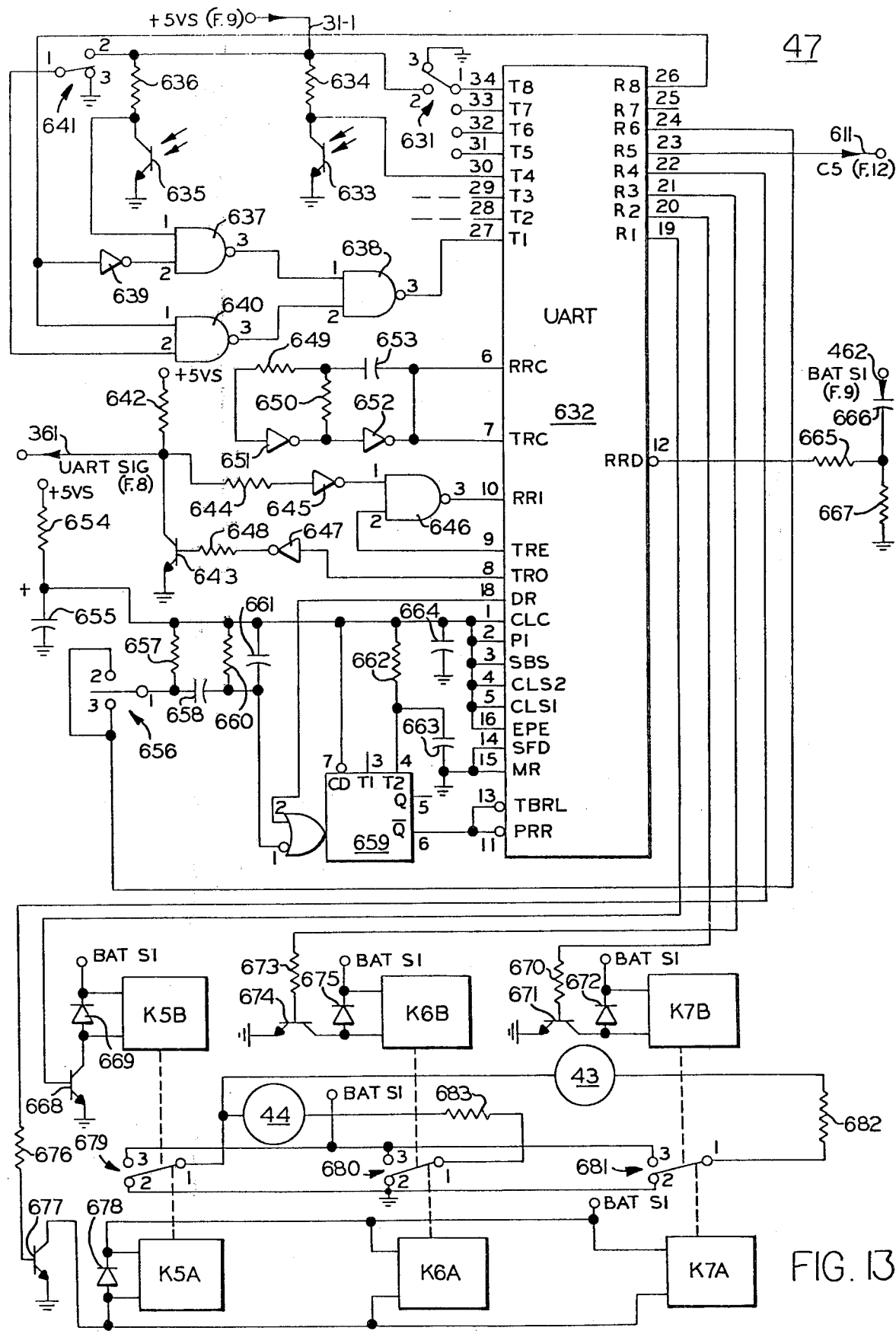
FIG. 13 is a schematic diagram of the remainder of the probe control shown in FIG. 2.

There is shown in FIG. 13 the remainder of the probe control circuit 47 of FIG. 2. Inputs to the circuit are the +5VS power supply voltage on the line 31-1, the UART SIG signal on the line 361, and the BAT S1 power supply voltage on the line 462. Outputs from the circuit are the UART SIG signal on the line 361 and the C5 control signal on the line 611.

The line 31-1 is connected to a fixed terminal 631-2 of a single pole, double throw switch 631. A second fixed terminal 631-3 is connected to the circuit ground potential and a movable terminal 631-1 is connected to a transmit data terminal 632-34 of a UART 632. The switch 631 is representative of three other such switches (not shown) each having a fixed contact connected to the line 31-1, a second fixed contact connected to the circuit ground potential, and a movable contact connected to one of the transmit input terminals 632-31, 632-32, and 632-33. The line 31-1 is also connected to a collector of an NPN photo transistor 633 through a resistor 634. The transistor 633 has an emitter connected to the circuit ground potential and a photo sensitive base for receiving light from one of the LEDs of the circuit of FIG. 12. The collector is connected to a transmit input 632-30 of the UART. The transistor 633 is representative of two other transistors connected to inputs 632-28 and 632-29.

The line 31-1 is connected to a collector of a photo transistor 635 through a resistor 636. The transistor 635 has an emitter connected to the circuit ground potential and the collector connected to an input 637-1 of a NAND 635. An output 637-3 is connected to an input 638-1 of a NAND 638. A receive output 632-26 is connected through an inverter 639 to an input 637-3 of the NAND 637. The output 632-26 is also connected to a input 640-1 of a NAND 640. The line 31-1 is connected to a fixed terminal 641-2 of a switch 641. A second fixed terminal 641-3 is connected to the circuit ground potential and a movable terminal 641-1 is connected to an input 640-2 of the NAND 640. The NAND 640 has an output 640-3 connected to an input 638-2 of the NAND 638. The NAND 638 has an output 638-3 connected to a transmit input 632-27.

The line 361 is connected to the +5VS power supply through a resistor 642 and to a collector of an NPN transistor 643 having an emitter connected to the circuit ground potential. The line 361 is connected through a resistor 644 and an inverter 645 to an input 646-1 of a NAND 646. The NAND 646 has an output 646-3 connected to a RR1 input 632-10 and an input 646-2 connected to a TRE output 632-9. A TRO output 632-8 is connected through an inverter 647 and a resistor 648 to a base of the transistor 643.

A pair of resistors 649 and 650 are connected in series across an inverter 651. An output of the inverter 651 is connected to an input of an inverter 652 having an output connected to a RRC input 632-6 and a TRC input 632-7. A capacitor 653 is connected from a junction of the resistors 649 and 650 to an output of the inverter 652.

A CRL input 632-1 is connected to the +5VS power supply through a resistor 654 and to the circuit ground potential through a capacitor 655. The input CRL is also connected to a P1 input 632-2, a SBS input 632-3, a CLS2 input 632-4, a CLS1 input 632-5, and an EPE input 632-16. A single pole, double throw momentary contact switch 656 has a pair of fixed contacts 656-2 and 656-3 which are connected together to a receive output 632-24. A movable contact 656-1 of the switch 656 is connected to the CRL input 632-1 through a resistor 657 and through a capacitor 658 to an inverting input 659-1 of a monostable multivibrator 659. The input 659-1 is also connected to the input CRL 632-1 through a resistor 660 connected in parallel to the capacitor 661.

A DR output 632-18 is connected to a non-inverting input 659-2 of the monostable multivibrator 659. A reset input 659-7 is connected to the CRL input 632-1. A second timing input 659-2 is connected to the input 632-1 through a resistor 662 and to the circuit ground potential through a capacitor 663. The input 632-1 is connected to the circuit ground potential through a capacitor 664 and a SFD input 632-14 and a MR input 632-15 are also connected to the circuit ground potential. The multivibrator 659 has an inverting output 659-6 connected to a TBRL input 632-13 and a DRR input 632-11.

An RRD input 632-12 is connected through a resistor 665 and a capacitor 666 to the line 462. The input 632-12 is also connected through the resistor 665 and a resistor 667 to the circuit ground potential.

A receive output 632-19 is connected to a base of an NPN transistor 668 having an emitter connected to the circuit ground potential. The transistor 668 has a collector connected to an anode of a diode 669 having a cathode connected in the BAT S1 power supply line. A K5 relay coil K5B is connected across the diode 669. A receive output 632-20 is connected through a resistor 670 to a base of an NPN transistor 671 having an emitter connected to the circuit ground potential. A collector of the transistor 671 is connected to an anode of a diode 672 having a cathode connected to the BAT S1 power supply line. A K7B relay coil of a K7 relay is connected across the diode 672. A receive output 632-21 is connected through a resistor 673 to a base of an NPN transistor 674 having an emitter connected to the circuit ground potential. The transistor 674 has a collector connected to an anode of a diode 675 having a cathode connected to the BAT S1 power supply line. A K6B relay coil of a K6 relay is connected across the diode 675. A receive output 632-22 is connected through a resistor 676 to a base of an NPN transistor 677 having an emitter connected to the circuit ground potential. The transistor 677 has a collector connected to an anode of a diode 678 having a cathode connected to the BAT S1 power supply line. A K5A relay coil of the K5 relay is connected across the diode 678. A receive output 632-23 is connected to the C5 control signal line 611.

The relay coils K5A and K5B control a movable contact 679-1 of the K5 relay. When the K5A coil is energized, the movable contact 679-1 will be moved into contact with a fixed contact 679-2 as shown. The fixed contact 679-2 is connected to the circuit ground potential. When the K5B relay coil is energized, the movable contact 679-1 will be moved into contact with a fixed contact 679-3 connected to the BAT S1 power supply.

A K6A relay coil is connected across the diode 678. When the K6A relay coil is energized, a movable contact 680-1 of the K6 relay is moved into contact with a fixed contact 681-2 which is connected to the circuit ground potential. When the K6B relay coil is energized, the movable contact 680-1 is moved into contact with a fixed terminal 680-3 connected to the BAT S1 power supply line.

A K7A relay coil is connected across the diode 678. When the K7A relay coil is energized, a movable contact 681-1 of the K7 relay is moved into contact with a fixed contact 681-2 which is connected to the circuit ground potential. When the K7B relay coil is energized, the movable contact 681-1 is moved into contact with a fixed contact 681-3 which is connected to the BAT S1 power supply line.

The DC filter motor 43 is connected between the movable contact 679-1 and a resistor 682 which is connected to the movable contact 681-1. The source motor 44 is connected between the movable contact 679-1 and a resistor 683 which is connected to the movable contact 680-1.

The UART 632 communicates with the UART 56 in the electronic unit over the line 361. The UART 632 controls the K5, K6, and the K7 relays which, in turn, control the motors 43 and 44 to position the filters and the shutters. The UART 632 also turns on the LED transmitters with the C5 control signal on the line 611 and controls the operation of the continue pawl switch 656. The switch 656 is disabled during the operation of the filters to prevent any interaction when the electronic unit is communicating with the probe. The UART 632 receives a signal from the switch (not shown) connected to the input 632-31 which generates a signal each time a filter is in position in the probe. Thus, the UART receives a signal indicating when the filters are rotating and how many times they have rotated. The switches (not shown) connected to the inputs 632-32 and 632-33 indicate whether the shutter for the Cd 109 source is opened or closed. The switches 631 and 641 indicate whether or not the shutter for the Fe 55 source is opened or closed. The brackets for holding the filters are coded in four predetermined positions with the presence or absence of holes for a determination of which filter is in position. The four predetermined positions are located in the light paths from the four LEDs to the four photo transistors represented by the transistors 633 and 635. Thus, the UART receives a binary coded decimal signal which represents the indentification of the filter which is in position.

The speed of operation of the UART is controlled by an oscillator formed from the inverters 651 and 652, the resistors 649 and 650 and the capacitor 653. The transistor 653, the inverters 645 and 647, and the NAND gate 646 enable the UART to operate over a single line. It receives signals through the inverter 645 and the NAND gate 646, and it transmits signals to the inverter 647 and the transistor 643. The request to interrogate the probe is received on the line 316 and the UART triggers the monostable multivibrator 659 to generate a slight delay. When the multivibrator times out, the UART transmits data back to the electronic unit on the line 361 concerning the position of the filters and the shutter indicating switches.

Figure 14:
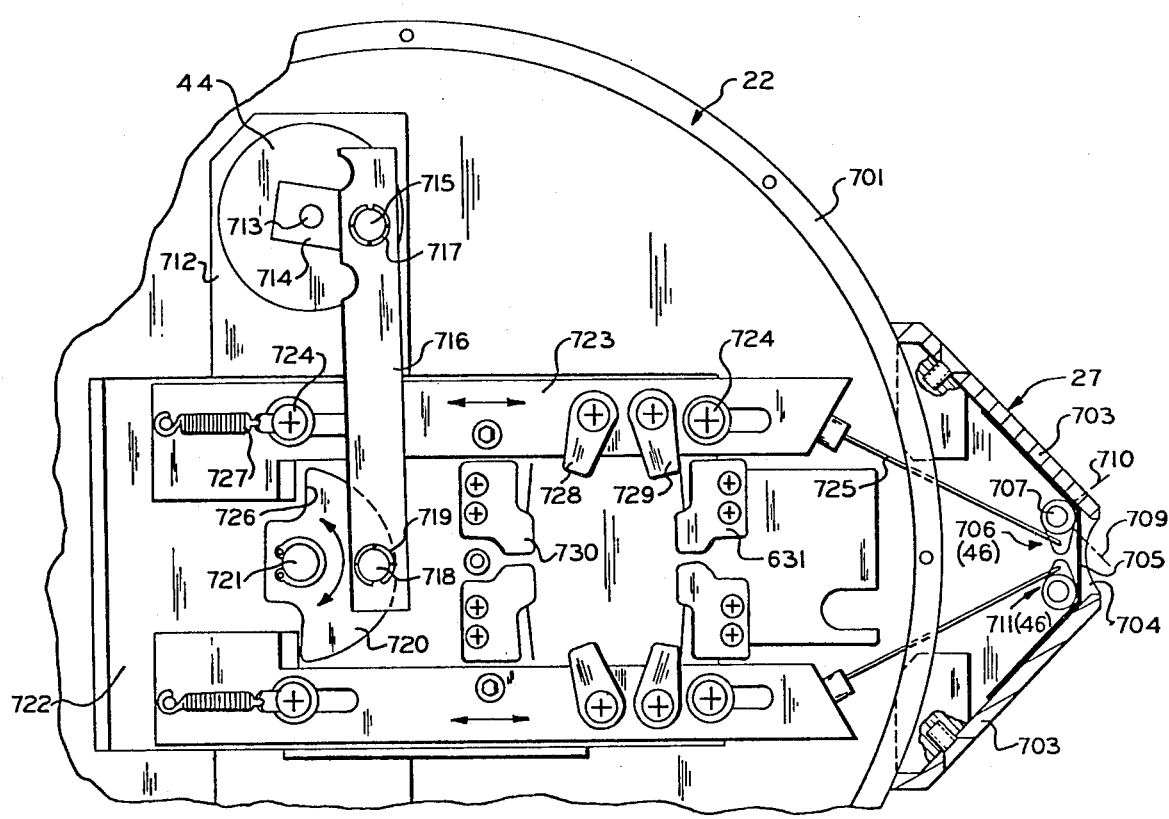
FIG. 14 is a fragmentary top plan view of the probe housing of FIG. 1 showing the source shutters and shutter drive mechanism.
Figure 15:
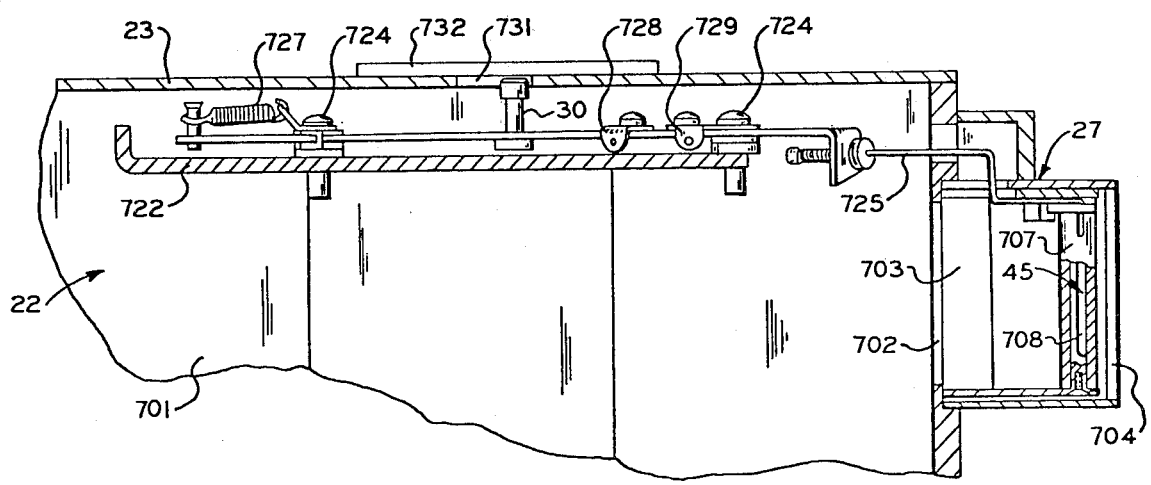
FIG. 15 is a fragmentary side elevational view of the probe housing of FIG. 1 showing the source shutters and shutter drive mechanism.

There is shown in FIG. 14 a top plan view of the probe housing of FIG. 1 with the top cover 23 and the top of the source housing 27 removed. In the interest of clarity, only the source shutters and the shutter drive mechanism are shown. There is shown in FIG. 15 a fragmentary side elevational view of the probe housing of FIG. 1 with only the source shutters and the shutter drive mechanism shown in the interest of clarity. The detector housing 22 includes a cylindrical side wall 701 in which is formed an aperture 702 for passing X-rays from the sample material to the radiation detector (not shown). The source housing 27 is attached to the outside of the side wall 701 by suitable means. The source housing 27 has a body formed as a right triangular prism, triangular in cross-section, with a pair of side walls 703 tapering from an open base at the aperture 702 to a tip forming a narrow aperture 704. The aperture 702 is covered by a "window" which typically is formed of facing sheets of Mylar material and polypropylene material which are attached to the inside surfaces of the side walls 703. The window material is pervious to the radiation from the source and the sample.

A first shutter means 706 (one of the shutters 46 of FIG. 2) has a generally tubular body 707 which is rotatably mounted at its ends to the top and bottom of the source housing 27. A generally tubular collimator and source holder 708 is mounted inside the shutter 707 and is stationary with respect to the source housing. Radiation from the source 45 can only exit the collimator through a port along a line 709. The radiation can only exit the shutter through a shutter port along a line 710 which is generally positioned at right angles with respect to the line 709 when the shutter is in the closed position as shown in FIG. 14. As will be discussed, when the shutter is rotated in a clockwise direction by the shutter drive motor 44, the shutter port is in axial alignment with the collimator port and radiation from the source exits through the window 705 along the line 709.

A second shutter means 711 (one of the shutters 46 of FIG. 2) is positioned adjacent the other side of the aperture 704 and includes a different radiation source. For example, the shutter means 706 can include an Fe 55 radiation source while the shutter means 711 can include a Cd 109 radiation source.

The shutter drive motor 44 is mounted on a motor support bracket 712 and has an output shaft 713 which is connected to one end of an output arm 714. The other end of the output arm 714 has a pin 715 connected thereto which extends through an aperture in one end of a link arm 716. The link arm 716 is retained on the pin 715 by a snap ring 717. The other end of the link arm 716 is attached to a pin 718, extending through an aperture in the arm, by a snap ring 719. The pin 718 is connected at the periphery of a semi-circular cam 720 which is rotatably mounted on a shaft 721 attached to a shutter plate 722. A shutter slide 723 is mounted for longitudinal movement on the shutter plate 722 by a pair of guides 724 attached to the shutter plate 722 and extending through elongated apertures formed in the shutter slide 723.

The end of the shutter slide 723 adjacent the source housing 727 has one end of a wire link 725 attached thereto, the other end of the wire link being attached to an arm extending from the side of the shutter 707. When the drive motor 44 is rotated in the counterclockwise direction as viewed in FIG. 14, the cam 720 is also rotated in the counterclockwise direction. An end 726 of the cam 720 engages the camming surface on the shutter slide 723 and forces the shutter slide in a direction away from the source housing 27. The movement of the shutter slide 723 is transmitted through the wire link 725 to rotate the shutter 707 to line up the shutter port with the collimator port. When the motor 44 is rotated back to the position shown in FIG. 14, a return spring 727, connected between the guide 724 adjacent the cam 720 and the shutter slide 723, returns the shutter slide 723 and the shutter 707 to the positions shown.

Attached to the shutter slide 723 are a pair of switch actuating cams 728 and 729. A pair of limit switches, the switch 631 and a switch 730, are attached to the shutter plate 722. The switch 631 is shown in FIG. 13 in its unactuated state. When the shutter 707 is closed, as is shown in FIG. 14, the switch 631 is actuated by the switch cam 729 to apply the voltage from the line 31-1 to the terminal 632-26 of the UART 632 of FIG. 13. Although not shown, the switch 730 is connected in a manner similar to the switch 631 to the input 632-25. As shown in FIG. 14, the switch 730 is not actuated and therefore, would generate the circuit ground potential to the UART 632. The combination of these two signals indicates that the shutter 707 is in the closed position. When the shutter drive motor 44 actuates the shutter slide 723, the switch cam 728 is moved into contact with the actuating arm of the switch 730 and the cam 729 is moved out of contact with the actuating arm of the switch 631. Thus, the switches 631 and 730 will reverse their signals to indicate to the UART 632 that the shutter 707 is in the open position. The second shutter means 711 is actuated in a similar manner and includes similar limit switches for indicating the position of the shutter associated therewith.

The shutter slide 723 has a generally upstanding source shutter position tag 30 attached thereto. The upper end of the tag 30 extends into an elongated aperture 731 formed in the top cover 23 of the probe housing. The movement of the shutter slide 723 moves the tag 30 in the aperture 731 between marked "off" and "on" positions which are shown in FIG. 1. A transparent cover 732 can be attached to the upper surface of the top cover 23 to cover the aperture 731. Although not shown, a similar aperture is provided for the other shutter position tag which is attached to the shutter slide for the other radiation source.

Figure 16:
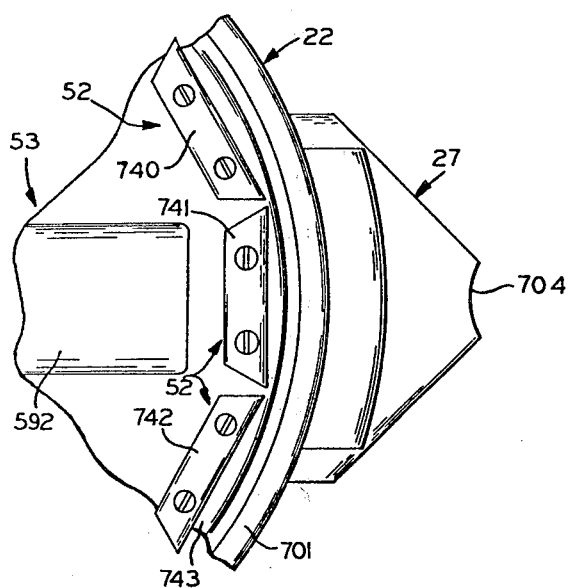
FIG. 16 is a fragmentary top plan view of the probe housing of FIG. 1 showing the radiation detector and filter brackets.

There is shown in FIG. 16, a fragmentary top plan view of the probe housing of FIG. 1 showing the placement of the radiation detector 53 and the filters 52. The radiation detector 53 includes the photomultiplier tube 592 which is positioned to receive X-rays which pass through the aperture 704 and window in the tip of the source housing 27 and through the aperture in the side wall 701 of the detector housing. A plurality of filters 52 include the filter brackets 740, 741, and 742. The brackets are attached to a disc 743 which is rotated beneath the radiation detector 592.

Figure 17:
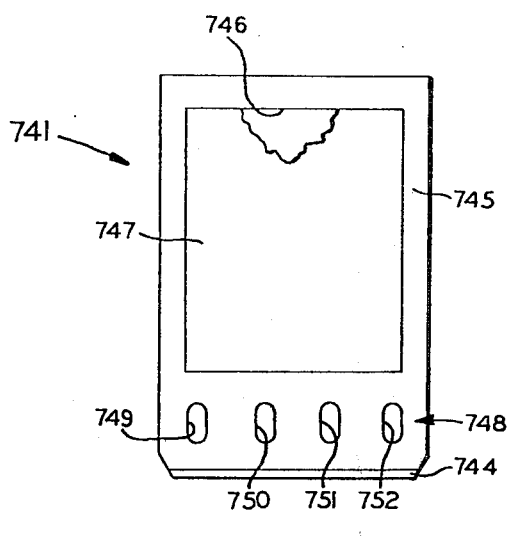
FIG. 17 is a side elevational view of one of the filter brackets of FIG. 16.

The bracket 741 is shown in a side elevational view in FIG. 17. The bracket 741 is generally L-shaped with a relatively short lower leg 744 attached to the upper surface of the disc 743 by suitable fastners. A generally upstanding leg 745 has a generally rectangular aperture 746 formed therein for receiving a sheet of filter material 747. Each of the filter brackets retains a sheet of different filter material for preferentially passing only the spectral lines of a selected element typically found in the materials analyzed. The bracket 741 also has an indentification means area 748 located between the lower leg 744 and the lower edge of the aperture 746. The area 748 can have from zero to four apertures 749 through 752 formed therein. The presence or absence of one of the apertures generates a binary coded signal in cooperation with one of the photodiodes and its associated photo transistor as shown in FIG. 13. There are sixteen different combinations of blocked and open apertures which can be utilized to identify the particular sheet of filter material which is located between the radiation detector 592 and the sample of material which is positioned at the tip of the source housing 27.

Figure 18:
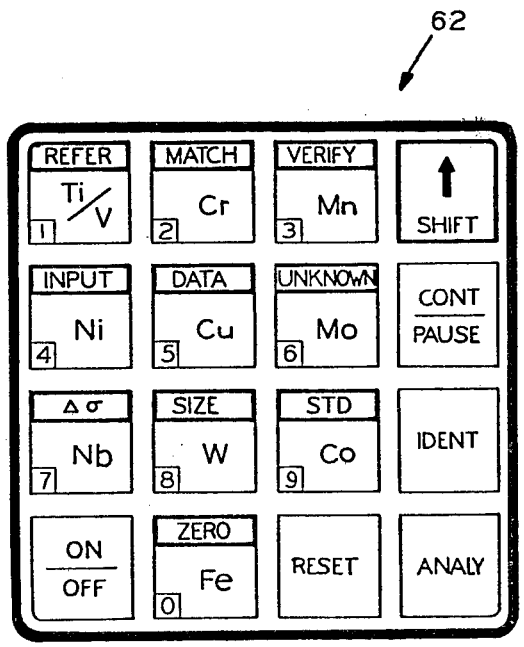
FIG. 18 is a plan view of the electronic unit keyboard of FIG. 2.

There is shown in FIG. 18 a plan view of the electronic unit keyboard of FIG. 2. The apparatus combines a well established analytical technique, radioisotope X-ray flourescence with microelectronics to accomplish several measurement objectives. The primary objectives are: verification of alloy grade or type and, composition analysis of a large number of engineering alloys. All measurements can be made with a sample in a variety of physical forms such as pipe, plate, weld and welding material, machine parts, castings, etc. The X-ray flourescence method is a nondestructive method which allows for measurement of many elements with high precision. Alloy identification is accomplished by recognizing the unique combination of several elements in narrowly specified composition ranges. Accurate quantitative analysis is achieved by making appropriate corrections for inter-element matrix effects.

The material to be analyzed is exposed for a few seconds to radiation from one of the radioisotope sources. The atoms of some of the elements of the material are caused to flouresce and emit X-rays which are characteristic of the element. The detector system separates X-rays coming from the sample into discrete energy regions and, from a measure of the intensity in each region, determines the element concentration. The energy regions correspond to the elements: Ti, V, Cr, Mn, Fe, Co, Ni, Cu, Nb, Mo and W are effectively analyzed. The central processor unit 58 coordinates the operation of the probe with the electronics unit according to instructions contained in the permanent memory. All essential calibration data is stored in this memory. In addition, a second memory is used for data processing and storage of standardization and other factors pertaining to special modes of operation.

The basic modes of operation are alloy identification and analysis. Each mode can be modified for a selected precision sample size comparision, and for other measurement conditions, through the touch-type keyboard 62 on the instrument panel of the electronic unit. Alloy identification is initiated by depressing the IDENT key. The probe is placed in position and the remote switch 656 is actuated. After approximately twenty seconds, if the measured data matched that of one of the library alloys, the alloy type is registered on the display 61. The number of alloys stored in the memory can exceed more than one hundred and includes most engineering alloys of importance. The apparatus enables the determination of the percent content of the elements shown on the keyboard. The content of the elements Ti, V, Cr, Ni, Cu, Nb, Mo and W can be displayed immediately after the identification measurement. These and other elements can also be analyzed specifically to a higher precision with matrix compensation based on the identification data. Alternatively, the alloy type to be analyzed can be entered through the keyboard so that even single element determination can be made with matrix compensated accuracy. A typical analysis takes between ten and twenty seconds. The element symbol is displayed along with the percent content.

Each mode of measurement can be modified by one of the four selectable levels of precision, and one of several size compensation routines. For example, the size compensation feature would correct for undersized samples and non-standard probe-to-sample air gap distances as might be presented by some weld configurations of a non-contact measurement on a high temperature surface. The effect on alloy identification of statistical variations in the measured X-ray intensities is automatically factored into the decision making process. The chance of a mistaken identity is estimated to be less than one in one hundred. As for elemental analysis, the precision depends on the element content and the alloy types. Some typical precision values for common alloys are shown in the following table. Precision can be improved by a factor of three when utilizing one of the increased precision modes. Accuracy is usually equal to the precision.

| TABLE OF PRECISION VALUES | |
|---|---|
| ALLOY TYPE | TYPICAL PRECISIONS |
| Low Alloy Steel | ±0.02% (Ti, V, Mo, Nb) |
| (e.g. 2.25 Cr, 1 Mo) | ±0.1% (Cr) |
|  | ±0.3% (Mn) |
| Stainless Steel | ±0.03% (Ti, V, Mo, Nb) |
| (e.g. SS304/316) | ±0.3% (Cr, Mn) |
|  | ±0.5% (Fe, Co, Ni, Cu) |
| Nickel Alloys | ±0.04% (Ti, V, Mo, Nb, W) |
| (e.g. Inconel 625, Hasteloy X) | ±0.2% (Ni) |
|  | ±0.35% (Cr, Mn, Cu) |
|  | ±0.55% (Fe, Co) |

Figure 19:
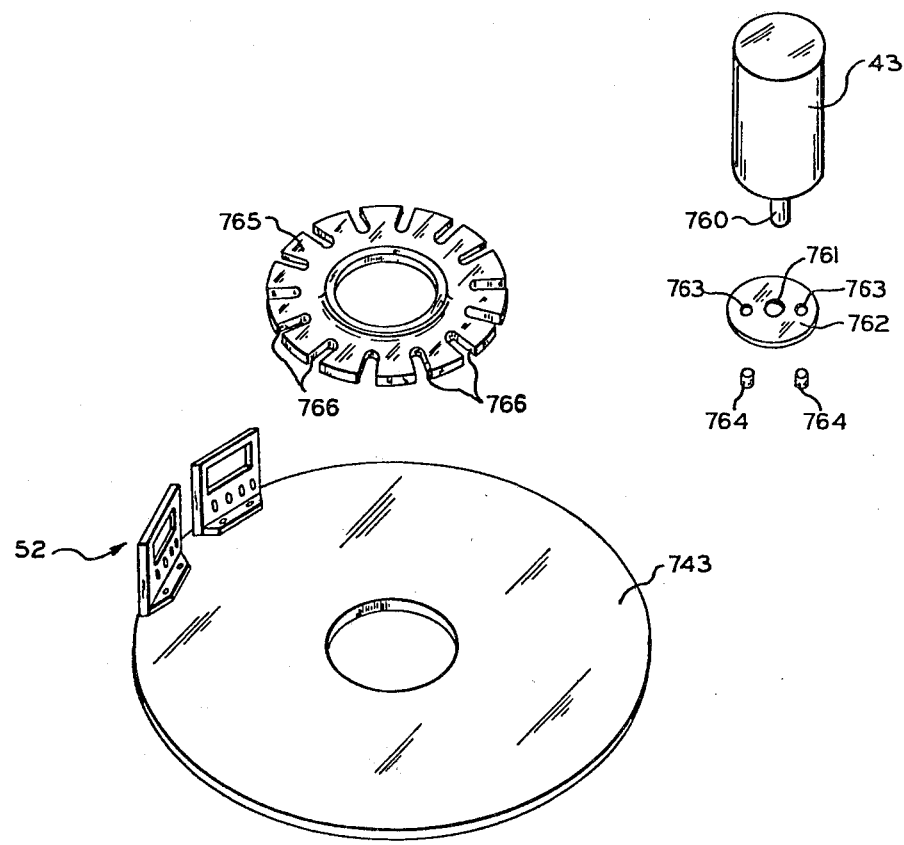
FIG. 19 is an exploded perspective view of the filter drive mechanism including the filters and filter motor of FIG. 2.

There is shown in FIG. 19 an exploded perspective view of the filter drive mechanism of the present invention. The filter drive motor 43 has an output shaft 760 which is retained in a centrally disposed aperture 761 formed in a drive wheel 762. The drive wheel 762 also has a pair of apertures 763 formed therein which are spaced equidistant on either side of the central aperture 761. Each of a pair of drive pins 764 is retained in one of the apertures 763 and extends above the surface of the drive wheel 762 opposite the surface facing the drive motor 43.

A geneva wheel 765 is attached to the filter bracket disc 743 for rotation about a common axis on a bearing (not shown). The periphery of the geneva wheel 765 has a plurality of slots 766 formed therein. The drive motor 43 and drive wheel 762 are positioned such that the drive pins 764 engage alternate ones of the slots 766 as the drive motor 43 rotates the drive wheel 762. Thus, during each one-half revolution of the drive wheel 762 the geneva wheel 765 and the filter bracket disc 743 are rotated a portion of one complete revolution to replace one of the filters 52 with an adjacent one of the filters.

Although the invention has been described in terms of specified embodiments which are set forth in detail, it should be understood that this is by illustration only and that the invention is not necessarily limited thereto, since alternative embodiments and operating techniques will become apparent to those skilled in the art in view of the disclosure. Accordingly, modifications are contemplated which can be made without departing from the spirit of the described invention.

What is claimed and desired to be secured by Letters Patent is:

1. In an apparatus for analyzing a sample of material by the X-ray fluorescence method having means responsive to X-ray radiation from the sample for generating a plurality of groups of sample signals each group representing the spectral lines and energy intensity in a predetermined one of a plurality of energy regions of a different element, an electronic unit comprising: first means for storing the groups of sample signals; second means for storing a plurality of groups of known signals, the known signals of each group representing the spectral lines and energy intensities in the plurality of predetermined energy regions of a different known material; means connected to said first and second means for storing for comparing the sample signals stored in said first means with the known signals in the corresponding energy regions stored in said second means and for generating an identification signal representing the identity of the sample of material when the sample signals stored in the first means correspond to said known signals of one of said groups stored in said second means; and means connected to said means for comparing and responsive to said identification signal for generating an indication of the identity of the sample of material.

2. The electronic unit according to claim 1 wherein said first and second means for storing include random access memories.

3. The electronic unit according to claim 1 wherein said means for comparing includes a microprocessor.

4. The electronic unit according to claim 1 wherein said means for generating an indication includes a multi-digit liquid crystal display means.

5. The electronic unit according to claim 4 wherein said identification signal is generated as a series of binary signals and said means for generating an indication includes shift register means responsive to said binary signals for generating output signals to drive said liquid crystal display means to generate a visual indication of the identity of the material sample.

6. The electronic unit according to claim 4 wherein said means for generating an indication includes a twisted ring counter means responsive to said identification signal for generating AC output signals to drive said liquid crystal display means to generate a visual indication of the identity of the material sample.

7. The electronic unit according to claim 6 wherein said liquid crystal display means generates a backplane signal and said means for generating an indication includes means responsive to said backplane signal for enabling said twisted ring counter means to generate said AC output signals.

8. The electronic unit according to claim 1 including means connected to said second means for storing for generating signals representing the spectral lines and energy intensities of known materials to said second means for storing.

9. The electronic unit according to claim 8 wherein said means for generating signals includes a keyboard.

10. In an apparatus for analyzing a sample of material by the X-ray fluorescence method having a probe unit for generating a plurality of sample signals each representing an element in the material sample and an electronic unit responsive to the signals for generating an indication of the identity of the material sample, the electronic unit comprising: first means for storing the plurality of sample signals generated by the probe unit; second means for storing a plurality of groups of signals representing the elements of known materials; means connected to said first and second means for storing for comparing the sample signals stored in said first means for storing with each of said groups of signals stored in said second means for storing and generating an identification signal representing the identity of the sample when the signals correspond to the signals in one of said groups of signals; and means connected to said means for comparing and responsive to said identification signal for generating an indication of the identity of the material sample, said means for generating an indication including a multiple-digit liquid crystal display means, said means for generating an indication further including a twisted ring counter means responsive to said identification signal for generating AC output signals to drive said display means to generate a visual indication of the identity of the material sample.

* * * * *